(12) United States Patent
Hosmalin et al.

(10) Patent No.: US 9,932,556 B2
(45) Date of Patent: Apr. 3, 2018

(54) METHOD FOR IN VITRO DIFFERENTIATION OF BLOOD CIRCULATING CELLS INTO NEURONAL-LIKE CELLS AND APPLICATIONS THEREOF

(71) Applicants: Centre National de la Recherche Scientifique (CNRS), Paris (FR); Universite Paris Descartes, Paris (FR); Institut National De La Sante Et De La Recherche Medicale (INSERM), Paris (FR); Assistance Publique—Hopitaux De Paris, Paris (FR)

(72) Inventors: Anne Hosmalin, Paris (FR); Vincent Feuillet, Paris (FR); Marie-Odile Krebs, Paris (FR); Thérèse Jay, Montreuil (FR); Alfredo Bellon, Coral Gables, FL (US)

(73) Assignees: Centre National de la Recherche Scientifique (CNRS), Paris (FR); Universite Paris Descartes, Paris (FR); Institut Ntaitonal de la Sante et de la recherche Medicale (INSERM), Paris (FR); Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 14/515,884

(22) Filed: Oct. 16, 2014

(65) Prior Publication Data

US 2015/0111225 A1 Apr. 23, 2015

(30) Foreign Application Priority Data

Oct. 17, 2013 (EP) .................................. 13306428

(51) Int. Cl.
*C12N 5/0775* (2010.01)
*C12N 5/0793* (2010.01)
*G01N 33/50* (2006.01)

(52) U.S. Cl.
CPC ......... *C12N 5/0619* (2013.01); *C12N 5/0665* (2013.01); *G01N 33/5055* (2013.01); *G01N 33/5058* (2013.01); *G01N 33/5073* (2013.01); *C12N 2500/12* (2013.01); *C12N 2500/30* (2013.01); *C12N 2501/105* (2013.01); *C12N 2501/13* (2013.01); *C12N 2501/22* (2013.01); *C12N 2501/385* (2013.01); *C12N 2501/999* (2013.01); *C12N 2503/00* (2013.01); *C12N 2503/02* (2013.01); *C12N 2506/115* (2013.01); *C12N 2533/52* (2013.01); *G01N 2500/10* (2013.01); *G01N 2800/28* (2013.01)

(58) Field of Classification Search
CPC .................................................. C12N 5/0665
See application file for complete search history.

(56) References Cited

U.S. PATENT DOCUMENTS

| 8,663,987 B2 * | 3/2014 | Kadouri ............... C12N 5/0668 435/366 |
| 2003/0059939 A1 | 3/2003 | Page et al. |
| 2004/0136973 A1 | 7/2004 | Huberman et al. |

FOREIGN PATENT DOCUMENTS

| EP | 1 605 040 | 7/2009 |
| WO | WO 03/083092 | 10/2003 |
| WO | WO 2011/091048 | 7/2011 |

OTHER PUBLICATIONS

Aldridge et al., *The use of total protein stains as loading controls: an alternative to high-abundance single protein controls in semi-quantitative immunoblotting*, 172(2) J. Neurosci. Methods 250-254 (Jul. 30, 2008).
Aras et al., *Assessment of Cell Viability in Primary Neuronal Cultures*, Supplement 44 Current Protocols in Neuroscience 1-15 (Jul. 2008).
Bellon, *New genes associated with schizophrenia in neurite formation: a review of cell culture experiments*, 12 Molecular Psychiatry 620-629 (2007).
Da Silva et al., *Breaking the Neuronal Sphere: Regulation of the Actin Cytoskeleton in Neuritogenesis*, 3 Nature 694-70 (Sep. 2002).
Feng et al., *Ghrelin and obestatin modulate growth hormone-releasing hormone release and synaptic inputs onto growth hormone-releasing hormone neurons*, 34 European Journal of Neuroscience 732-744 (2011).
Fuss et al., *Isolation of Whole Mononuclear Cells from Peripheral Blood and Cord Blood*, Supplement 85 Current Protocols in Neuroscience 1-8 (Apr. 2009).
Goslin et al., *Experimental Observations on the Development of Polarity by Hippocampal Neurons in Culture*, 108 The Journal of Cell Biology 1507-1516 (Apr. 1989).
Grassi et al., *Monocyte-derived dendritic cells have a phenotype comparable to that of dermal dendritic cells and display ultrastructural granules distinct from Birbeck granules*, 64 Journal of Leukocyte Biology 484-493 (Oct. 1998), Jun. 22, 2016.
Kodama et al., *Neurogenic potential of progenitors derived from human circulating CD14+ monocytes*, 84 Immunology and Cell Biology 209-217 (2006).
Lanza et al., *Structural and functional features of the CD34 Antigen: an update*, 15(1) Journal of Biological Regulators and Homeostatic Agents 1-13 (2001).
Okubo et al., *Decreased prefrontal dopamine D1 receptors in schizophrenia revealed by PET*, 385 Nature 634-636 (Feb. 13, 1997).

(Continued)

*Primary Examiner* — Robert C Hayes
(74) *Attorney, Agent, or Firm* — Buchanan Ingersoll & Rooney PC

(57) ABSTRACT

The present invention relates to a method for in vitro differentiation of a population of blood circulating cells, such as monocytes and preferably pluripotent macrophages derived therefrom, into cells displaying functional and phenotypic neuronal characteristics. The invention further encompasses neuronal-like cells obtainable according to the present method, compositions comprising said cells, and applications thereof.

9 Claims, 19 Drawing Sheets

(56) References Cited

OTHER PUBLICATIONS

Rüschenschmidt et al., *Functional Properties of ES Cell-Derived Neurons Engrafted into the Hippocampus of Adult Normal and Chronically Epileptic Rats*, 46(Suppl. 5) Epilepsia 174-183 (2005).
Seta et al., *Derivation of multipotent progenitors from human circulating CD14+ monocytes*, 38 Experimental Hematology 557-563 (2010).
Wiles, *Embryonic Stem Cell Differentiation in Vitro*, 225 Methods of Enzymology 900-918 (1993).
Ying et al., *Assessment of Cell Viability in Primary Neuronal Cultures*, Supplement 13 Current Protocols in Neuroscience pp. 1-17 (2000).
Zhao et al, *A human peripheral blood monocyte-derived subset acts as pluripotent stem cells*, 100(5) PNAS 2426-2431 (Mar. 4, 2003).
European Search Report issued in European Patent Application 13 30 6428 completed on Mar. 18, 2014.

\* cited by examiner

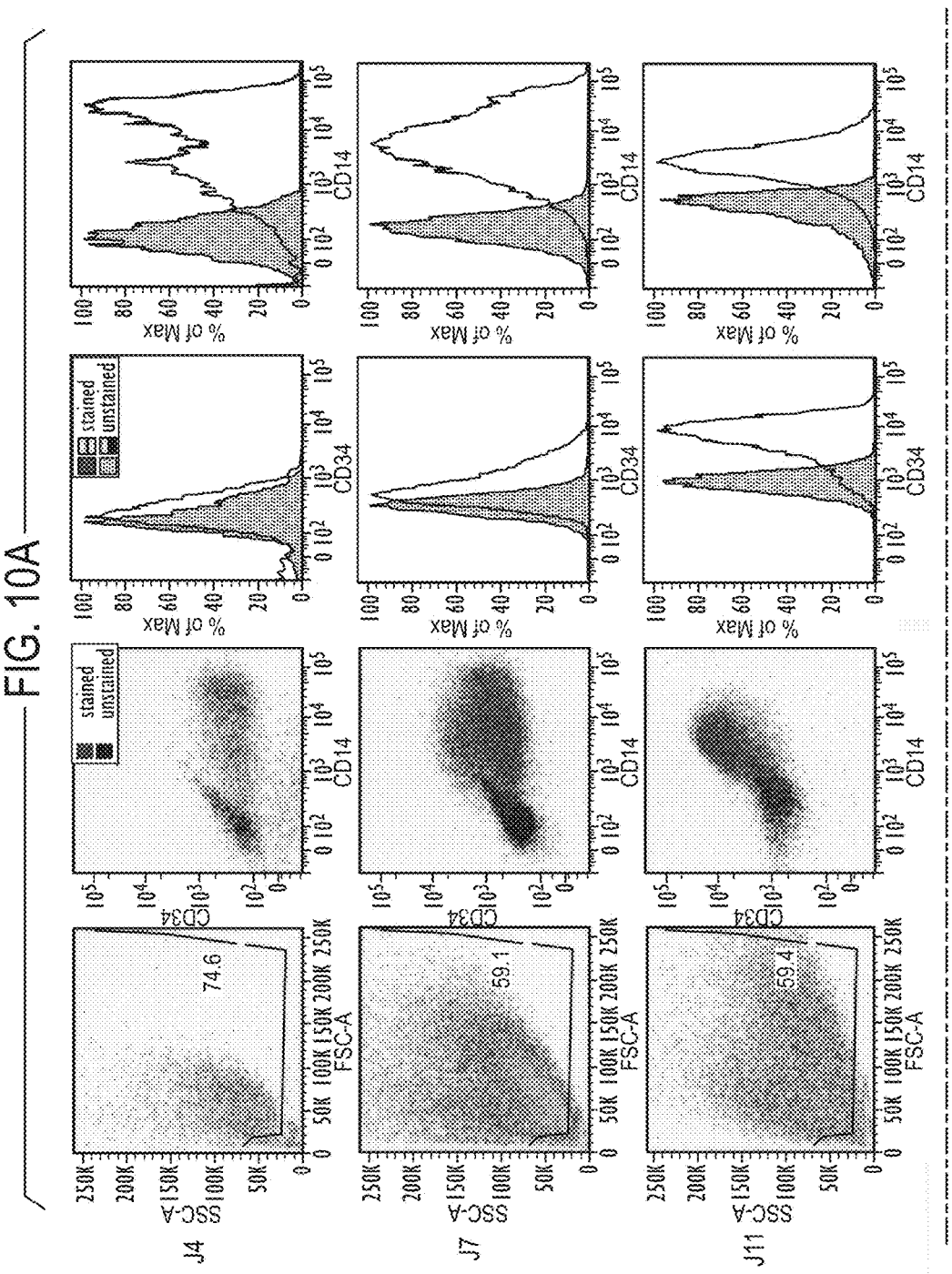

METHOD FOR IN VITRO DIFFERENTIATION OF BLOOD CIRCULATING CELLS INTO NEURONAL-LIKE CELLS AND APPLICATIONS THEREOF

CROSS-REFERENCE TO RELATED APPLICATION

This application claims priority to European Patent Application No. 13306428.7, filed on Oct. 17, 2013, the content of which is incorporated herein by reference in its entirety for all purposes.

INTRODUCTION

The present invention relates to a method for in vitro differentiation of a population of blood circulating cells, such as monocytes and preferably pluripotent macrophages derived therefrom, into cells displaying a functional neuronal phenotype. The invention further encompasses neuronal-like cells obtainable according to the present method, compositions comprising said cells, and applications thereof.

Given the limited regenerative capability of adult neuronal cells, repairing the central nervous system (CNS) has become one of the frontiers that medical science has yet to conquer.

Developing cell populations that can reconstitute a functional neural network has thus become crucial, not only to establish neuron-replacement therapies, but also to study the normal physiological behavior of neurons, to diagnose neurological injuries or conditions, such as psychiatric disorders, and to develop cell-based assays for screening pharmacological or toxicological agents.

In recent years, a great deal of interest has been focused on differentiating pluripotent stem cells (PSC) into neuronal-like cells. To date, numerous therapeutic transplantations have been performed exploiting various types of fetal tissue as the source of donor material (Ruschenschmidt et al, 2005). However, the use of PSC isolated from human fetuses, umbilical cords, or embryonic tissues from fertilized eggs has raised many practical, ethical and legal issues. Notably, such approach increases the transmission of infectious disease(s); furthermore, the inaccessibility of the PSC limits their availability as a cell source for transplantation therapies.

To overcome the above limitations, notably the derivation of patient-specific cells, one approach has thus consisted in exploiting the differentiation capacity of autologous somatic or stem cells, preferably isolated from an accessible tissue.

In this context, Page et al. (US 2003/0059939) attempted to induce neuronal differentiation by co-culturing in vitro somatic cells in the presence of cytoskeletal, acetylation, and methylation inhibitors; however, the resulting neuronal phenotype was only transient, as after removal of the priming agent, the neuronal morphology and established synapses were not maintained for longer than a few weeks, and complete conversion to a fully functional and stable neuronal-like cell has never been demonstrated.

Alternatively, Wernig et al. (WO 2011/091048) proposed to produce neuronal-like cells by transducing stem cells or somatic cells such as fibroblasts, with lentiviral vectors expressing various transcription factors. However, the neuronal differentiation rate provided by this method was extremely low (below 7%) and raised as well critical safety issues, which impair the use of these cells in cell-replacement therapy. In addition, fibroblasts used in such method may only be obtained by a biopsy, which is invasive for the patient.

Others reported that specific subsets of blood circulating cells can act as pluripotent stem cells. Based on this discovery, Zhao et al. (2003) attempted to differentiate circulating monocytes into various cell lineages, by undergoing an intermediate pluripotent state. In particular, the authors managed to isolate monocytes-derived pluripotent macrophages from peripheral blood cells—which they described as replicating progenitors of macrophages with a fibroblastic morphology ("f-macrophages")—and stimulated their neuronal differentiation through NGF treatment. However, despite demonstrating the expression of various neuronal markers such as NSE (Neuron-specific enolase), NF (Neurofilament) and MAP-1B (Microtubule-associated protein 1B) and a neuronal-like morphology, the authors did not address whether the differentiated cells were functional, i.e. exhibited an electrical activity.

Likewise, Kodama et al. (2006) attempted to induce neuronal differentiation by co-culturing monocyte-derived multi-potential cells with primary cultures of rat neurons. However, the differentiation rate of this method was low (about 20%), and despite expressing neuronal markers such as neurofilament, Hu, NeuN (Neuronal nuclear antigen), MAP-2 (Microtubule-associated protein 2) or tubulin-beta 3, and a neuronal-like morphology, the cells did not exhibit any electrophysiological activity typical of neurons.

Of upmost importance, while developing the method according to the invention, the inventors attempted to reproduce, without success, the above methods described by Zhao et al. (2003) and Kodama et al. (2006): none of them enabled the generation of cells with a morphology resembling the one of neurons, and even less so of cells exhibiting any electric activity of neuronal phenotype. Furthermore, the cells generated by these two methods exhibited a low expression of neuronal markers.

There is thus still a need for a method that can reproducibly generate in vitro neuronal populations, which are fully functional, and which can be easily used as tools for medical research, drug screening, diagnosis and/or treatment of various neurological disorders and diseases.

The present invention addresses the above discussed need in the art.

In particular, the inventors have surprisingly and unexpectedly discovered that the stimulation of monocytes-derived pluripotent macrophages, by a specific combination of growth factors and antioxidants, namely BHA (Butylated hydroxyanizole), RA (Retinoic Acid), IGF-1 (insulin growth factor-1), NT-3 (Neurotrophin-3), and, optionally of an agent capable of stimulating calcium influx, such as KCl enabled their differentiation into neuronal-like cells.

Contrary to the methods described in the prior art, notably based on the differentiation of blood circulating cells, the method developed by the inventors enables the obtention of cells that exhibit not only a morphology and a marker expression typical of neurons but also, most importantly, an electrical activity of a neuronal phenotype: these cells can thus be referred herein as functional neuronal-like cells. In particular, the inventors demonstrated that the cells obtained by this particular process can receive and transmit action potentials, and are thus fully capable of neuronal communication.

Furthermore, the neuronal differentiation rate provided by the present method is higher than the one described in the prior art, as it can reach up to 40%. Thanks to this high differentiation rate, a large number of neuronal-like cells can be generated, in a short time period.

A high reproducibility is also provided herein, as neuronal-like cells were successfully derived by the inventors from blood circulating cells isolated from 40 individuals.

Besides, neuronal-like cells can be easily generated by the method of the invention from a mere blood sample of a subject, as pluripotent macrophages used herein can be simply derived from monocytes isolated from blood.

For the above reasons, the differentiation method of the invention and the population of functional neuronal-like cells obtained by said method are particularly useful for diagnostic, therapeutic and screening purposes.

Notably, the present method can be used to rapidly and reliably diagnose neurological disorders, from a mere blood sample, thereby avoiding using conventional, cumbersome and potentially invasive diagnostic methods such as biopsies or magnetic resonance imaging (MRI).

Functional neuronal-like cells obtained by the present method may also be used to replace deficient neuronal cells from an individual affected by a neurological disorder, notably a neurodegenerative disorder. The possibility to use autologous cells for such therapeutic purpose, such as blood circulating cells, prevents any health risk that is usually associated with possible transmission of viral or bacterial infections of foreign origin, and the risks of immuno-rejection. It further permits to avoid modulating the patient immune response before cell transplant.

Therapeutic compounds of interest may also be identified by using healthy or pathological neuronal-like cells generated by the present method, in particular compounds that maintain, stimulate and/or restore neuronal growth and/or neuronal function.

The present invention thus provides for the first time, a method for in vitro differentiation of a population of pluripotent macrophages into a population of fully functional neuronal-like cells. The invention further provides a population of neuronal-like cells obtainable by said method, a pharmaceutical composition comprising said population, a screening method for identifying compounds capable of maintaining, stimulating and/or restoring neuronal growth and/or function, as well as a method and a kit for diagnosing or prognosing a neurological disorder.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as "Culture of Animal Cells: A Manual of Basic Technique and Specialized Applications" (2010), 6th Edition, by Freshney, and "Embryonic Stem Cell Differentiation in Vitro" (1993) by Wiles.

Nevertheless, with respect to the use of different terms throughout the current specification, the following definitions more particularly apply.

"Comprising" or "containing" means, without limitation, the inclusion of the referent and does not exclude the presence of any other element. For example, "a method comprising the step of x" encompasses any method in which x is carried out, whether x is the only step in the method or only one of the steps, no matter how many other steps are included, and no matter how simple or complex x may be in comparison to the other steps. Likewise, "a composition comprising x and y" encompasses any composition that contains x and y, no matter what other components may be present in the composition.

The term "about" means that the value of reference can vary within a certain range depending on the margin of error allowed, which may be easily determined by one skilled in the art.

By "macrophage", or "Mϕ", it is meant herein a CD14+ (cluster of differentiation 14 positive) peripheral blood mononuclear cell (PBMC), which is capable of phagocytosis, lymphocyte stimulation, and cytotoxicity. Preferably, a macrophage according to the invention is further positive for at least one biomarker selected from the group consisting of the cell surface antigen markers CD11b, CD18, CD45, CD115 (also known as colony stimulating factor 1 receptor or macrophage colony-stimulating factor receptor), CD68 (i.e. clusters of differentiation 11 b, 18, 45, 115 and 68), HLA-DR (Human leukocyte antigen DR), and which may produce at least one of the cytokines IL-1beta, IL-6, IL-10, IL-12 p70 (i.e. Interleukins 1 beta, 6, 10 and 12 p70), and/or TNF-alpha (Tumor necrosis factor alpha), upon activation by one or several foreign substance(s) such as e.g. a microbial product.

According to the following aspects and embodiments of the invention described herein, the term "pluripotent macrophage" refers to a macrophage as defined above that is capable to give rise to at least two or more cell types of a mammalian organism, such as a human or an animal.

Preferably, a "pluripotent macrophage" according to the invention displays a fibroblastic morphology ("f-macrophage"), is capable of self-renewal and expresses elevated levels of the CD34 surface antigen marker (i.e. it is CD34+), as well as low levels of the CD14 surface antigen marker (i.e. it is CD14+). "Self-renewal", "proliferation" or "division" refers herein to the ability to produce replicate daughter cells.

Advantageously, one skilled in the art may refer to the description of these pluripotent cells provided by Seta et al. (2010) and Zhao et al. (2003). Even more preferably, a "pluripotent macrophage" according to the invention is as defined by Zhao et al. (2003), i.e. by comparison to standard macrophages ("s-Mϕ"), a "pluripotent macrophage" ("f-Mϕ") exhibits:

reduced levels of IL-10, TNF-alpha, TNF-RII, HLA-DR, HLA-DQ, leptin and PPAR gamma 2;
increased levels of CD34;
reduced levels of lipids;
a reduced cytotoxicity; and
an increased lymphocyte stimulation.

By "a population of cells", it is meant herein at least two cells. Thus, by "a population of pluripotent macrophages" according to the invention, it is meant at least two pluripotent macrophages as defined above.

The term "neural cell", "neuronal cell", "nerve cell" or "neuron" refers herein to a cell displaying a neuronal phenotype, which forms the basic unit of the nervous system of a subject.

By "neuronal phenotype", it is meant the expression of at least one neuronal marker, the presence of a neuronal morphology, and the display of an electrical activity.

Examples of typical neuronal markers include, without limitation, Nestin, NeuN (Neuronal nuclear antigen), MAP (Microtubule-associated protein) such as MAP-2, NF (Neurofilament) such as NF-H or NF-M, GAP-43 (Growth associated protein 43), PSD-95 (Postsynaptic density protein 95), AMPA (α-amino-3-hydroxy-5-methylisoazol-4-propionate) receptor, D1 receptor (Dopamine 1 receptor), Tyrosine Hydroxylase (TH), HuD, Peripherin, Tubulin-beta 3, CDK5 (Cyclin-dependent kinase 5), MacMARCKS (Myristoylated alanine-rich C kinase substrate-related protein), MARCKS (Myristoylated alanine-rich C kinase substrate protein), Neuron Specific *Enolase* (NSE), Parvalbumin, PGP9.5 (Protein Gene Product 9.5), STEP (Striatal-enriched tyrosine phosphatase), STOP (Stable tubule-only polypeptide), Tau, CD-90 (Cluster of differentiation 90), Encephalopsin, GAD 65 (Glutamate Decarboxylase), LINGO-1 (Leucine rich repeat and Ig domain containing 1), $Na^+/K^+$ ATPase subunits, 4.1 G, Acetylcholinesterase, ACK1 (Activated Cdc42-associated kinase 1), ABP (AMPA Receptor Binding Protein), ARG3.1 (Activity-regulated cytoskeleton-associated protein), ARP2 (Actin-related protein 2), E-Cadherin, N-Cadherin, Calcyon, Catenin alpha or beta, Caveolin, CHAPSYN-110, Clathrin light chain, Cofilin, CPLX1 (Complexin 1), Contactin-1, CRIPT (Cysteine-rich PDZ-binding protein), CSP (Cysteine String Protein), Dynamin 1 and 2, Flotillin-1, Fodrin, GRASP (GRP1-associated scaffold protein), GRIP1 (General receptor for phosphoinositides 1), Homer, Mint-1, Munc-18 (Mammalian uncoordinated-18), NSF (N-ethylmaleimide-sensitive factor), PICK1 (Protein interacting with PRKCA 1), RAB4, Rabphillin 3A, SAD A or B, SAP-102 (Synapse-associated protein 102), SHANK1a (SH3 and multiple ankyrin repeat domains 1a), SNAP-25 (Synaptosomal-associated protein, 25 kDa), Snapin, Spinophilin, Stargazin, Striatin, SYG-1, Synaptic Vesicle Protein 2A or 2B, Synapsin 1, Synaptobrevin, Synaptojanin, Synaptophysin, Synaptotagmin, synGAP (Synaptic Ras GTPase activating protein), Synphilin-1, Syntaxin 1, 2, 3, 4, Synuclein alpha, VAMP-2 (Vesicle-associated membrane protein 2), VAChT (Vesicular Acetylcholine Transporter), VGAT (Vesicular GABA transporter), VGLUT (Vesicular Glutamate Transporter) 1, 2 or 3, and VMAT (Vesicular Monoamine Transporter) 1 or 2.

Examples of neuronal morphological or structural components, include, without limitation, a soma (or nerve cell body) and neurites. A soma is the central part of a neuron, it contains the nucleus of the cell, and most commonly exhibits a rounded and well defined shape. Neurites are thin extensions from the soma; they may be of different length, but in well differentiated cells these extensions are longer than twice the soma size. Mature forms of neurites are axons and dendrites. A typical neuronal cell possesses one soma, along with one axon and/or one or several dendrites. Dendrites are multiple branching extensions arising from the soma; while an axon is a cable-like branching projection that emerges as well from the soma and extends for up to tens of thousands of times the diameter of soma in length. Advantageously, the terminal end of an axon comprises synapses which allow communication with other neurons by electrical signaling. Typically, the mechanism underlying neuronal communication between these structural components is as follows: an electrical signaling is emitted by a neuron and transmitted via its axon, notably via synapses, to neighboring neurons; the electrical signaling is then received by the neighboring neurons by the soma and dendrites.

Neurons vary in shape and size, and may be classified into three main sub-groups based on their number of neurites:

a "unipolar" or "pseudo-unipolar" neuron typically refers to a neuron with only one neurite (i.e. the dendrite and axon are fused together);

a "bipolar" neuron typically refers to a neuron with a single axon and a single dendrite, which are orientated on opposite ends of the soma;

a "multipolar" or "stellar" neuron typically refers to a neuron with a single axon and more than two dendrites.

These sub-groups of neurons may further be subdivided into short, long, thick or thin neurons. For example, a bipolar neuron may be referred as a short bipolar neuron if its neurites length is inferior to twice the size of its soma. By contrast, a bipolar neuron may be referred as a long bipolar neuron is its neurites length is equal or superior to twice the size of its soma. Advantageously, in order to characterize the shape and size of neurons, one may refer to the classification established by Martin (2012), Blumenfeld (2011) Palay et al. (1977), Da Silva et al. (2002), Goslin et al. (2007) and/or Bellon et al. (2007).

By "electrical activity", "electrical signaling", "electrical excitability" or "electrophysiological activity", it is meant herein the capacity of receiving, integrating and/or transmitting electric signal(s), such as action potential(s). The term "action potential" refers to a short-term variation in the electrical potential on the cell surface in response to a stimulation which leads to the rapid transmission of an electrical impulse that travels across the cell membrane in order to activate surrounding cells. It is well known in the art that the presence of such "electrical activity" underlies the presence of voltage-gated ion channels embedded in the cellular membrane, that allow the neuron to generate and propagate an electric signal such as an action potential, which may lead in return to the release of a neurotransmitter. Examples of voltage-gated ion channels include, without limitation, sodium, calcium, potassium, and chloride ions channels. Methods for measuring electrical activity in neurons are well-known in the art. Examples of such method include, without limitation, patch-clamping and imaging relying on voltage- or calcium-sensitive fluorescent dyes. For a complete review of neuronal electrophysiology, one skilled in the art may refer to the manual "The Neuron: Cell and Molecular Biology: Cell and Molecular Biology" (2001) by Levitan et al.

By "functional neuronal-like cell", "neuron-like cell", or "nerve-like cell" according to the present invention, it is meant herein a cell displaying a neuronal phenotype as defined above, but which does not naturally form the basic unit of the nervous system of a subject. In the context of the present invention, and as further described below, functional neuronal-like cells are preferably derived from blood circulating cells. These neuronal-like cells are referred herein as being functional as they exhibit an electrical activity as defined above. More particularly, said cells have the capacity not only of receiving and integrating electrical signals, but also of transmitting said electric signal(s), so as to allow communication with the surrounding neuronal cells.

As used herein the term "monocyte" refers to a CD14+ (cluster of differentiation 14 positive) and CD34− (cluster of differentiation 34 negative) peripheral blood mononuclear cell (PBMC), which is capable of differentiating into macrophage(s) and dendritic cell(s) upon activation by one or several foreign substance(s) such as e.g. a microbial product. In particular, a monocyte expresses elevated levels of the CD14 surface antigen marker. Preferably, a monocyte according to the invention is further positive for at least one biomarker selected from the group consisting of the cell surface antigen markers CD64, CD93, CD180, CD328 (also known as sialic acid-binding Ig-like lectin 7 or Siglec7), and CD329 (sialic acid-binding Ig-like lectin 9 or Siglec9) (i.e.

clusters of differentiation 64, 93, 180, 328 and 329), as well as the peanut agglutinin protein (PNA).

The term "culture medium", "growth medium" or "cell medium" according to the invention encompasses any medium comprising growth-promoting components, and which is suitable for the maintenance and proliferation of the cells to be cultured (i.e. grown).

By "conditioned medium", "conditioned culture medium" or "conditioned growth medium" according to the invention, it is meant a culture medium in which cells have been grown for a period of time, such as for about 4 to 13 days, and which therefore contains metabolites, growth factors and/or extracellular matrix components secreted by said cells which may assist with cell proliferation and differentiation. As commonly known in the art, a conditioned medium is preferably mixed with fresh culture medium. A particularly preferred conditioned medium according to the invention is a conditioned medium of pre-grown peripheral blood mononuclear cells (PBMCs); such conditioned medium can be referred herein as a PMBCs-conditioned medium.

The term "exogenous factor" (as opposed to endogenous factors) refers herein to any molecule that does not form part of cells, such as growth factors and antioxidants, and that is provided to said cells from an external source.

By "agent capable of stimulating calcium influx", it is meant herein an exogenous factor that, when contacted with one or several cells, notably cells grown in a culture medium, leads to an increase of the intracellular calcium level of said cells. Preferably, if said cells are being differentiated into neuronal-like cells, said agent may facilitate the differentiation process, for example by promoting the expression of neuronal markers and by inducing neurite outgrowth. Examples of agents capable of stimulating calcium influx, include, without limitation, potassium chloride (KCl) and ionomycin. A particularly preferred agent capable of stimulating calcium influx according to the invention is KCl.

By "final concentration of x", it is meant herein the concentration of x in the environment, such as culture medium, after its addition into said environment.

Additional definitions are provided throughout the specification.

The method proposed by the present invention induces blood circulating cells in culture to progress through stages of neuronal differentiation, and gives rise to cells exhibiting a neuronal phenotype, referred herein as functional neuronal-like cells.

So, in a first aspect, the present invention is directed to a method for in vitro differentiation of a population of pluripotent macrophages into a population of functional neuronal-like cells, wherein:
1) a population of pluripotent macrophages is grown in a culture medium; and
2) exogenous factors BHA (Butylated hydroxyanizole), RA (Retinoic Acid), IGF-1 (Insulin growth factor-1) and NT-3 (Neurotrophin) are added to the culture medium of step 1).

The neuronal differentiation rate obtained by the present method can reach up to 40%. By contrast, if one or more of the above exogenous factors is omitted from the culture medium, or replaced with other exogenous factor(s) such as IGF-2 (Insulin growth factor-2), FGF (Fibroblast growth factor), NGF (Nerve growth factor), BDNF (Brain-derived neurotrophic factor), Hydrocortisone, Valproic acid, Insulin and/or Metformin, almost no neuronal differentiation occurs: the neuronal differentiation rate will indeed at best reach up to 10%, which nevertheless is not reproducible in a consistent manner contrary to the method of the invention. Culturing a population of pluripotent macrophages in a neuronal medium, without any exogenous factor, did not either stimulate neuronal differentiation.

Thus, the specific inventive combination of the exogenous factors BHA, RA, IGF-1, and NT-3 represents the minimal combination of exogenous factors necessary to achieve the differentiation of pluripotent macrophages into fully functional neuronal-like cells as defined above.

As previously mentioned, it was discovered that specific subsets of blood circulating cells, such as monocytes, can differentiate into pluripotent macrophages (Zhao et al., 2003). Accordingly, the population of pluripotent macrophages used in step 1) of the above method is preferably derived from a population of monocytes, such as human monocytes, and may therefore be referred herein as monocytes-derived pluripotent macrophages. In the context of the present invention, it may be particularly advantageous to derive pluripotent macrophages from monocytes, as the latter can be easily collected from the blood sample of a subject.

Thus, in a preferred embodiment, the above method further comprises a prior step of differentiating a population of monocytes into a population of pluripotent macrophages.

Preferably, the differentiation of said population of monocytes into a population of pluripotent macrophages is obtained by:
a) growing a population of monocytes in a culture medium;
b) adding the exogenous factor M-CSF (Macrophage colony-stimulating factor) to the medium of step α).

Preferably, the M-CSF of step b) is added to the medium of step α) at a final concentration comprised between about 25 ng/ml and about 100 ng/ml; preferably between about 35 ng/ml and about 75 ng/ml; and most preferably is 50 ng/ml.

Advantageously, the density at which the population of monocytes is grown in step α) is comprised between about 70,000 cells/cm$^2$ and about 350,000 cells/cm$^2$, preferably between about 80,000 cells/cm$^2$ and about 300,000 cells/cm$^2$, and most preferably is about 110,000 cells/cm$^2$. For example, 1.2 million monocytes may be grown per each 9.6 cm$^2$ well of a 6-well tissue culture plate, 550,000 monocytes may be grown per each 3.1 cm$^2$ well of a 12-well tissue culture plate, and/or 6 million monocytes may be grown per each 25 cm$^2$ tissue culture flask.

Thus, accordingly, the density at which the population of pluripotent macrophages is grown in step 1) is preferably comprised between at least about 70,000 cells/cm$^2$ and about 350,000 cells/cm$^2$, preferably between at least about 80,000 cells/cm$^2$ and about 300,000 cells/cm$^2$, and most preferably is of at least about 110,000 cells/cm$^2$. For example, 1.2 million pluripotent macrophages may be grown per each 9.6 cm$^2$ well of a 6-well tissue culture plate, 550,000 pluripotent macrophages may be grown per each 3.1 cm$^2$ well of a 12-well tissue culture plate, and/or 6 million pluripotent macrophages may be grown per each 25 cm$^2$ tissue culture flask.

The density of cells to be grown can nevertheless vary between species. Additionally, optimal density can vary depending on culture conditions and source of cells. It is within the skill of ordinary person in the art to determine the optimal density for a given set of culture conditions and source of cells.

Typical culture media that can be used in the above method are easily available and well-known in the art. Examples of such media include, without limitation, Dulbecco's Modified Eagle's Medium® (DMEM), DMEM F12

Medium®, Eagle's Minimum Essential Medium®, F-12K Medium®, Iscove's Modified Dulbecco's Medium® and RPMI-1640 Medium®. Many media are also available as low-glucose formulations, with or without sodium pyruvate. A preferred culture medium to be used in the above method is Dulbecco's Modified Eagle's Medium® (DMEM), and most particularly, Dulbecco's Modified Eagle's Medium® (DMEM) High Glucose, GlutaMAX™.

Also contemplated in the present method is supplementation of the culture medium with mammalian sera, which contains cellular factors and components that can be necessary for cell maintenance and proliferation. Examples of sera include, without limitation, fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid. A particularly preferred culture medium to be used in the above method is DMEM (such as High Glucose, GlutaMAX™), supplemented with fetal bovine serum (FBS), such as 1% to 30% FBS-supplemented DMEM medium, preferably 5 to 20% FBS-supplemented DMEM medium, and most preferably 10% FBS-supplemented DMEM medium.

Yet, advantageously, the culture medium used in the present method comprises a conditioned medium. For example, as described above, the culture medium can comprise a conditioned medium mixed with fresh culture medium, preferably in a 2:1 or a 1:1 ratio. In particular, if said population of pluripotent macrophages is derived from a population of monocytes as described above, the culture medium according to the present method preferably comprises a conditioned medium of pre-grown peripheral blood mononuclear cells (PBMC). Thus, most preferably, said conditioned medium is a conditioned 10% FBS-supplemented DMEM medium of pre-grown peripheral blood mononuclear cells (PBMC). As indicated above, the use of a conditioned medium may assist in cell proliferation and differentiation.

In a particularly preferred embodiment, the differentiation of said population of monocytes into said population of pluripotent macrophages is obtained by:
  a) growing said population of monocytes in a culture medium supplemented with M-CSF for about 4 days;
  b) replacing the culture medium of step α) with a conditioned medium, preferably a PBMC conditioned medium, mixed with fresh culture medium; and
  c) further growing the cells in the medium of step b) for at least 3 days.

In a preferred embodiment of the above method, the population of cells used in the present invention is maintained and grown in the culture medium, while being attached a solid support such as a tissue culture flask or plate, preferably via extracellular matrix components. Indeed, pluripotent cells often require additional factors that encourage their attachment to a solid support, such as type I and type II collagen, poly-D and poly-L-lysine, polyornithine, chondroitin sulfate, fibronectin, "superfibronectin" and fibronectin-like polymers, gelatin, thrombospondin and vitronectin. Preferably, said population of cells are maintained and grown in the culture medium as defined above on a solid support coated with fibronectin, "superfibronectin" or a fibronectin-like polymer. Most preferably the solid support is coated with fibronectin at a concentration of at least $20_{14}$/ml. The use of fibronectin may also assist in cell proliferation and differentiation.

According to an advantageous embodiment of the above method, the recited exogenous factors of step 2) are sequentially added to the culture medium of step 1). Preferably, said exogenous factors are added in the following order:
  i) first, BHA;
  ii) second, RA; and
  iii) third, IGF-1 and NT-3.

This sequential addition of exogenous factors facilitates the gradual neuronal differentiation of the population of pluripotent macrophages, thus improving the yield and the robustness of the present method.

Still preferably, IGF-1 and NT-3 are added simultaneously in step iii).

Particularly preferred concentrations of exogenous factors used in steps i) to iii) as described above are as follows.

The BHA final concentration in step i) is preferably comprised between about 50 nM and about 200 nM, more preferably between about 50 nM and about 100 nM, and most preferably is 50 nM.

The RA final concentration in step ii) is preferably comprised between about 10 µM and about 20 µM, more preferably between about 12 µM and about 18 µM, and most preferably is 16 µM.

The IGF-1 final concentration in step iii) is preferably comprised between about 5 ng/ml to about 250 ng/ml, more preferably from about 5 ng/ml and about 50 ng/ml, and most preferably is 12.5 ng/ml.

The NT-3 final concentration in step iii) is preferably of up to about 30 ng/ml, and most preferably is 30 ng/ml.

These preferred concentrations of exogenous factors have been identified by the inventors as the optimal concentrations allowing the differentiation of the population of pluripotent macrophages into a population of functional neuronal-like cells, without altering the cell viability and the neuronal differentiation rate. It is within the skill of ordinary person in the art to select the concentration of each exogenous factor to be used in the present method among the above defined concentrations. In particular, the skilled person in the art will readily understand that the different concentration ranges of said exogenous factors may be combined, as required.

In the most preferred embodiment of the above method, the BHA final concentration in step i) is 50 nM, the RA final concentration in step ii) is 16 µM, the IGF-1 final concentration in step iii) is 12.5 ng/ml, and the NT-3 final concentration in step iii) is 30 ng/ml.

Yet, in a preferred embodiment, step 2) of the above method further comprises an intermediate step, wherein the BHA final concentration is adjusted before step iii) to a concentration comprised between about 50 µM and about 100 µM.

Preferably, the BHA final concentration may be adjusted between steps ii) and iii) by:
  α) replacing the culture medium of step ii) with fresh culture medium supplemented with about 50 µM to about 100 µM BHA; and
  β) adding RA to the medium of step α) at a final concentration as described above.

More preferably, the BHA final concentration in step α) is comprised between about 50 µM and about 75 µM, and most preferably is 50 µM. Yet, preferably, the RA final concentration in step β) is comprised between about 10 µM and about 20 µM, preferably between about 12 µM and about 18 µM, and most preferably is 16 µM. As indicated above, it is within the skill of ordinary person in the art to select the concentration of each exogenous factor to be used in the present method among the above defined concentrations.

In a preferred embodiment, the addition of each or all of the exogenous factor in step 2) of the method of the invention further comprises the step of replacing the culture medium of the previous step with fresh culture medium supplemented with the same concentration of exogenous factor(s) as previously added.

Such intermediate step may be useful to eliminate any toxic by-product secreted by the cells and to provide fresh nutrients. The skilled person will easily determine the frequency and the time at which such step should be performed during the growth of the cells.

As an illustrative example, before the addition of RA in step ii), the culture medium of step i) can be replaced with fresh culture medium supplemented with about 50 nM to about 200 nM BHA.

Likewise, before the addition of IGF-1 and NT-3 in step iii), the culture medium of step ii) can be replaced with fresh culture medium supplemented with about 50 μM to about 100 μM BHA, and with about 10 μM to about 20 μM RA.

In a preferred embodiment, step 2) of the above method further comprises the optional step of: iv) adding at least one agent capable of stimulating calcium influx to the medium of step iii).

The addition of said agent may indeed induce cellular depolarization, as well as stimulate the neurite outgrowth of the cells undergoing a neuronal differentiation. The inventors notably discovered that the use of said agent may improve the reproducibility of the present method, as well as the differentiation rate.

As described above, said agent capable of stimulating calcium influx is preferably KCl or ionomycin, and most preferably is KCl.

The final concentration of agent capable of stimulating calcium influx should be sufficient to induce the entry of calcium into the cells, which can be easily determined by one skilled in the art. For example, the KCl final concentration in step iv) is preferably comprised between about 10 mM and about 40 mM, more preferably between about 20 mM and about 30 mM, and most preferably is 25 mM. Alternatively, ionomycin concentration in step iv) is preferably comprised between about 250 ng/ml and about 1 μg/ml, more preferably between about 350 ng/ml and about 750 ng/ml mM, and most preferably is 500 ng/ml.

In a preferred embodiment, the above method further comprises one or more further steps, wherein:
the cell phenotypes present at the different stages of the cellular growth are identified by analyzing specific cell markers, and
the stage of cellular growth at which the required exogenous factor and optional agent capable of stimulating calcium influx is added to the culture medium is selected based on the detection of a specific cell phenotype.

The presence or absence of specific cell markers can be easily assessed by methods well-known in the art, such as by FACS (fluorescence-activated cell sorting) or microscopy, which therefore need not be further detailed herein.

For illustrative purposes, if the cell phenotype is determined by FACS, said phenotype can said to be CD14− if the median relative fluorescence intensity (RFI) for said antigen marker is preferably below 10; and/or said phenotype can said to be CD34− if the median relative fluorescence intensity (RFI) for said antigen marker is preferably below 2. Alternatively, said phenotype may be determined based on mean relative fluorescence intensity (RFI); e.g. a cell phenotype can said to be CD34− if the mean relative fluorescence intensity (RFI) for said antigen marker is preferably below 3. It should nevertheless be noted that said numerical values are only provided as a representative example; those values are therefore not limiting to the invention, and do not preclude larger and/or smaller values, notably depending on the experimental settings and FACS instrument to be used.

Preferably, M-CSF is added to the culture medium in step b) when the cell phenotype is CD14+ and CD34− (i.e. monocytes as defined above).

Preferably, BHA is added to the culture medium in step i) when the cell phenotype is CD14+ and CD34+ (i.e. pluripotent macrophages as defined above).

Preferably, RA is added to the culture medium in step ii) when the cell phenotype is CD14+ and CD34+ and is positive for at least one neuronal marker. Preferably, the cellular expression level of said neuronal marker is inferior to the one of CD14 and/or CD34. Yet, still preferably, said marker is selected from the group consisting of Nestin, MAP-2 and Neurofilament.

Preferably, the BHA final concentration is adjusted before step iii) to a concentration comprised between about 50 μM and about 100 μM, when the cell phenotype is CD14+ and CD34+, and the cellular expression level of at least one neuronal marker, such as Nestin, MAP-2 or Neurofilament, is superior to the one of CD14 and/or CD34.

Preferably, IGF-1 and NT-3 are added to the culture medium in step iii) when the cell phenotype is CD14+ and CD34+, and the cellular expression level of at least one neuronal marker, such as Nestin, MAP-2 or Neurofilament, in the cells is preferably superior to the one of CD14 and/or CD34.

Preferably, the agent capable of stimulating calcium influx, such as KCl, is added to the culture medium in step iv) when the cell phenotype is CD14+ and CD34+; the cellular expression level of at least one neuronal marker, such as Nestin, MAP-2 or Neurofilament, is superior to the one of CD14 and/or CD34; and the cellular expression level of CD34 is inferior to the one of CD14.

Preferably, the neuronal differentiation process can be considered as completed when the cell phenotype is CD34−, CD14−, Nestin+, NeuN+, MAP-2+, Neurofilament+, GAP-43+, PSD-95+, AMPA+, Dopamine 1 receptor+, and Tyrosine Hydroxylase+.

In the most preferred embodiment, the method for in vitro differentiation of a population of pluripotent macrophages into a population of functional neuronal-like cells according to the present invention, comprises the steps of:
a) growing a population of monocytes in a culture medium supplemented with 50 ng/ml M-CSF for 4 days;
b) replacing the culture medium of step α) with a conditioned medium mixed with fresh culture medium;
c) further growing the cells in the culture medium of step b) for 3 days;
d) replacing the culture medium of step c) with a conditioned medium mixed with fresh culture medium, said mix being supplemented with 50 nM BHA;
e) further growing the cells in the culture medium of step d) for 3 days;
f) replacing the culture medium of step e) with conditioned medium mixed with fresh culture medium, said mix being supplemented with 50 nM BHA and 16 μM RA;
g) further growing the cells in the culture medium of step f) for 3 days;
h) replacing the culture medium of step g) with a conditioned medium mixed with fresh culture medium, said mix being supplemented with 50 µM BHA, 16 µM RA, 12.5 ng/ml IGF-1 and 30 ng/ml NT-3;

i) further growing the cells in the culture medium of step h) for 4 days;

j) adding 25 mM KCl to the culture medium of step i); and k) further growing the cells for at least 3 days, preferably for 3 to 8 days, in the culture medium of step j) until the cells display a CD34−, CD14−, Nestin+, NeuN+, MAP2+, Neurofilament+, GAP-43+, PSD-95+, AMPA+, Dopamine 1 receptor+ and Tyrosine Hydroxylase+ cell phenotype, thereby obtaining a population of functional neuronal-like cells as defined above.

Preferably, as indicated above, the conditioned medium used in the above steps is a PBMCs conditioned medium, as defined above.

Still, preferably, said cells are grown in the above steps on a solid support coated with fibronectin.

Yet, still preferably, once the differentiated population of functional neuronal-like cells is obtained and identified, it can be separated, if necessary, from its undifferentiated counterparts by methods well-known in the art. Such methods include, without limitation, FACS, ELISA, magnetic beads and combinations thereof. One preferred embodiment of the present invention contemplates the use of FACS to identify and separate cells based on cell-surface antigen expression.

Once established in culture, the population of functional neuronal-like cells can be used fresh or frozen and, if needed, stored as frozen stocks, using, for example, DMEM with 40% FCS and 10% DMSO. Other methods for preparing frozen stocks for grown cells are available to those skilled in the art.

The above method allowing the production of a population of functional neuronal-like cells can be particularly useful for therapeutic, screening and diagnostic purposes, as further described below. In this regard, according a preferred embodiment of the invention, the above method may be repeated until obtaining an effective amount of a population of functional neuronal-like cells useful for the therapeutic, screening and diagnostic purposes of the present invention.

Therefore, it is another aspect of the invention to provide a population of functional neuronal-like cells obtainable according to the method as described above.

Said population of functional neuronal-like cells preferably has at least one of the following features:
Nestin positive;
NeuN (Neuronal nuclear antigen) positive;
MAP-2 (Microtubule-associated protein 2) positive;
Neurofilament positive;
GAP-43 (Growth associated protein 43) positive;
PSD-95 (Postsynaptic density protein 95) positive;
AMPA (α-amino-3-hydroxy-5-methylisoazol-4-propionate) positive;
Dopamine 1 receptor positive; and
Tyrosine Hydroxylase positive.

Still preferably, said population of functional neuronal-like cells according to the invention further has a unipolar, bipolar or stellar shape, such as a short or long unipolar or bipolar shape, or a thick or thin stellar shape, as demonstrated in the experimental results further disclosed below.

According to another preferred embodiment of the invention, said population of functional neuronal-like cells is directly obtained according to the method described above.

Contrary to the neuronal-like cells described in the prior art, notably generated from blood circulating cells such as monocytes or pluripotent macrophages, the population of neuronal-like cells of the invention is functional, i.e. it displays an electrical activity. The population of functional neuronal-like cells of the invention is notably capable to display a pre-synaptic and a post-synaptic activity as demonstrated in the examples of the present application.

The population of functional neuronal-like cells of the present invention is thus particularly useful for therapeutic, screening and diagnostic purposes. For example, this population offers the possibility to replace deficient neuronal cells in patients afflicted by a neurological disorder, such as a neurodegenerative disease. Likewise, this population enables the skilled person to identify neuronal functional defects in patients by collecting a mere blood sample from a patient and by differentiating blood circulating cells from said sample into neuronal-like cells.

For therapeutic, screening and diagnostic purposes as further described below, the population of functional neuronal-like cells of the present invention can be used in its native state or can be engineered to express one or more molecules that may be useful for the applications of the invention.

For example, a population of functional neuronal-like cells that is transformed or transfected with exogenous nucleic acid such as DNA or RNA so as to secrete or release an active molecule may be used directly as a therapeutic, e.g. by implanting said engineered population to a subject at a region which is in communication with the targeted tissue or with cells in need of treatment. The term "subject" throughout the specification refers to a vertebrate, such as a human or an animal, preferably a human.

The population of functional neuronal-like cells of the present invention can be particularly useful for therapeutic purposes, notably for maintaining, stimulating and/or restoring neuronal growth and function of the nervous system that are altered in neurological disorders, such as in neurodegenerative diseases, neurodevelopmental diseases and traumas to the nervous system.

By "neurological disorders", it is meant herein any disorder of the body nervous system. Examples of neurological disorders according to the invention include, without limitation: cranial or cerebral trauma, aneurysms, strokes, heart attack, spinal cord injury, Alzheimer's disease, Parkinson's disease, Creutzfeldt-Jacob disease, kuru, Huntington's disease, multiple system atrophy, amyotropic lateral sclerosis (Lou Gehrig's disease), cerebral palsy, autism, demyelinating diseases including multiple sclerosis, monophasic demyelination, encephalomyelitis, multifocal leukoencephalopathy, panencephalitis, Marchiafava-Bignami disease, pontine myelinolysis, adrenoleukodystrophy, Pelizaeus-Maerzbacher disease, Spongy degeneration, Alexander's disease, Canavan's disease, metachromatic leukodystrophy, Krabbe's disease, spinal motor atrophy and Charcot-Marie-Tooth diseases, and neuropsychiatric disorders such as schizophrenia, attention deficit disorder (ADD), schizoaffective disorder, bipolar disorder, bipolar affective disorder, unipolar affective disorder, adolescent conduct disorder, autism, depression, and anxiety disorders. A particularly preferred neurological disorder according to the invention is schizophrenia.

It is thus another aspect of the present invention to provide a population of functional neuronal-like cells of the invention, as a medicament. Preferably, the invention relates to the population of functional neuronal-like cells of the invention, for use in the treatment of a neurological disorder. More precisely, the present invention relates to the use of the population of functional neuronal-like cells of the invention for manufacturing a medicament to treat a neurological disorder as described above.

In other words, the invention relates to a method for treating a neurological disorder comprising the step of administering an effective amount of the population of functional neuronal-like cells of the invention, to a subject in need thereof.

In a preferred embodiment, said population is transplanted within said subject.

In a preferred embodiment, said method for treating a neurological disorder comprises a prior step of obtaining a population of functional neuronal-like cells from a biological sample of the subject according to the in vitro differentiation method described above.

The term "treating, "treatment" or "treat" as used herein encompasses, among other, preventing, ameliorating, inhibiting, or curing a deficiency, dysfunction, disease, or other deleterious process, including those that interfere and/or result from a therapy.

An "effective amount" or "effective dose" as used herein is an amount which provides the desired effect. For therapeutic purposes, an effective amount is an amount sufficient to provide a beneficial or desired clinical result. Said effective amount may be provided all at once in a single administration or in fractionalized amounts in successive administrations. The preferred effective amount for a given application can be easily determined by the skilled person taking into consideration, for example, the size, age, weight of the subject, the type of injury and/or disease to be prevented or treated, and the amount of time since the injury or the disease began. In the context of the present invention, in terms of treatment, an effective amount of functional neuronal-like cells is an amount that is sufficient to maintain, stimulate and/or restore neuronal growth or function in a subject in need thereof.

Methods for administering cells into individuals are well known to those skilled in the art and include, but are not limited to, parenteral (referring to intravenous and intraarterial and other appropriate parenteral routes), intratheceal, intraventricular, intraparenchymal (including into the spinal cord, brainstem or motor cortex), intracranial, intrastriatal, intracisternal, intranigral, and any other way which allows the cells to migrate to the ultimate neuronal region in need of treatment. The administration method will often depend upon the disease to be treated. For example, in the case of Alzheimer's disease, Huntington's disease, and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of stroke, the preferred route of administration will depend upon where the stroke is, but may be directly into the affected tissue (which may be readily determined using MRI or other imaging techniques), or may be administered systemically. In a preferred embodiment of the present invention, the route of administration for treating an individual post-stroke is systemic, via intravenous or intra-arterial administration.

A neurological disorder as described above may preferably be treated by administering a pharmaceutical composition comprising the population of functional neuronal-like cells of the invention.

Thus, in another aspect, the present invention provides a pharmaceutical composition comprising an effective amount of the population of functional neuronal-like cells as described above, and at least one pharmaceutically acceptable carrier.

As used herein, the term a "pharmaceutically acceptable carrier" includes, without limitation, any solvent, buffer, salt solution, dispersion medium, coating, isotonic and absorption delaying agent, and the like, that is physiologically compatible. The type of carrier may be selected based upon the intended route of administration. Examples of pharmaceutically acceptable carriers include, without limitation, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, or preservatives.

The pharmaceutical composition according to the invention may further comprise at least one therapeutic or diagnostic agent. For example, the pharmaceutical composition of the invention may be administered together with, but not limited to, e.g., anti-inflammatory agents, anticoagulants, antithrombotics, neurotrophic factors such as BDNF (Brain-derived neurotrophic factor) or NT-3 (Neurotrophin-3), or even growth factors such as FGF (Fibroblast growth factor), NGF (Nerve growth factor), TGF-$\beta$ (Transforming growth factor-$\beta$), VEGF (Vascular-endothelial-cell growth factor) or IGF (insulin-like growth factor).

Thus, in another aspect, the present invention provides the pharmaceutical composition of the invention, as a medicament. Preferably, the invention relates to the pharmaceutical composition of the invention, for use in the treatment of a neurological disorder, such as schizophrenia. More precisely, the present invention relates to the use of the pharmaceutical composition of the invention for manufacturing a medicament to treat a neurological disorder as described above.

In other words, the invention relates to a method for treating a neurological disorder comprising the step of administering an effective amount of the pharmaceutical composition of the invention, to a subject in need thereof.

In a preferred embodiment, said pharmaceutical composition is transplanted within said subject.

In a preferred embodiment, said method for treating a neurological disorder comprises a prior step of obtaining a population of functional neuronal-like cells from a biological sample of the subject according to the in vitro differentiation method described above.

In order to treat a neurological disorder, it may be useful to identify therapeutic compounds by screening candidate compounds with a population of functional neuronal-like obtainable according to the in vitro differentiation method described above. The skilled person will immediately realize that the method of the invention is particularly convenient for such purpose. Indeed, thanks to the method of the invention, a population of healthy or pathological neuronal-like cells can be generated in a reliable manner, and in an amount sufficient to test and select compounds of interest. Such compounds may, for example, maintain the growth and/or the function of healthy neuronal-cells. Alternatively, such compounds may, for example, stimulate or restore the growth and/or the function of pathological neuronal cells.

Thus, in another aspect, the present invention relates to a method for screening compound(s) capable of maintaining, stimulating and/or restoring neuronal viability, neuronal growth and/or neuronal function, comprising the steps of:

a) contacting a candidate compound or combination of compounds with a population of neuronal-like cells obtainable according to the in vitro differentiation method of the invention described above; and
b) measuring neuronal viability, neuronal growth and/or neuronal function of said population of neuronal-like cells.

The term "neuronal viability" refers herein to the number of healthy (i.e. living) neuronal cells (regardless of phase around the cell cycle), based on a total neuronal cell sample.

By "neuronal growth", it meant herein an increase in process network density (e.g., axonal, dendritic, or neuritic growth, including branching), cell migration, or target innervation.

By "neuronal function", it is meant herein any function of the nervous system, e.g. neural chemical and electrical signaling, sensorimotor function or cognitive function.

Any of the above aspects may be measured using techniques well-known in the art, which therefore need not be further detailed herein. As an illustrative example, neuronal viability may be assessed according any of the methods described by Ying et al. (2001) and/or Aras et al. (2008).

According to a preferred embodiment, said method further comprises the step of:
c) comparing the level of neuronal viability, neuronal growth and/or neuronal function obtained in step b) with at least one control level.

Preferably, said control level is the level of neuronal viability, neuronal growth and/or neuronal function of a population of functional neuronal-like cells of one or more healthy subject(s).

Preferably, said control level is the level of neuronal viability, neuronal growth and/or neuronal function of a population of functional neuronal-like cells of one or more subject(s) affected by a neurological disorder.

As a population of neuronal-like cells can be easily obtained according to the in vitro differentiation method of the present invention, notably from a mere blood sample, it can be particularly useful to analyze a population of neuronal-like cells of a subject obtained by the method of the invention, for diagnostic or prognostic purposes. In particular, the method of the invention used for diagnostic or prognostic purposes allows to circumvent conventional, burdensome, or even invasive diagnostic or prognostic methods such as biopsy, magnetic resonance imaging (MRI), computed tomography (CT), intrathecal contrast-enhanced CT scan, electromyography or myelography.

Thus, in a further aspect, the invention provides a method for in vitro diagnosis or prognosis of a neurological disorder as described above, comprising the steps of:
a) obtaining a population of neuronal-like cells of a subject according to the in vitro differentiation method described above;
b) comparing the neuronal phenotype of the population of neuronal-like cells of said subject to one or more control neuronal phenotype(s); and
c) determining the presence or the absence of a neurological disorder in said subject, and/or determining or predicting the clinical outcome of said disorder in said subject, based upon the comparison in step b).

The term "diagnosing" or "diagnosis", as used in the context of the present invention, include the act or process of identifying the existence (or non-existence) and/or type of neurological disorder from which an individual may be suffering. "Diagnosing" can also refer to the act of distinguishing between one type of neurological disorder and one or more other types of neurological disorders, as described above.

By contrast, the term "prognosis" or "prognosing" as used herein refers to the determination or prediction of the likelihood that the condition of a patient suffering from a neurological disorder may progress, worsen, or even lead to death. The term "good prognosis" or "positive clinical outcome" means a desired clinical outcome. For example, in the context of the invention, a good prognosis may be an expectation of regression or disappearance of clinical signs or symptoms of said neurological disorder. The terms "poor prognosis" or "negative clinical outcome" on the other hand is used herein to mean an undesired clinical outcome. For example, in the context of the invention, a poor prognosis may be an expectation of a worsening of clinical signs or symptoms of the neurological disorder. Clinical outcome of a neurological disorder can be easily determined by one skilled in the art, and therefore need not to be further detailed herein.

Preferably, said control neuronal phenotype used in the above method is the neuronal phenotype of a population of neuronal-like cells of one or more healthy subject(s), which is obtainable according to the in vitro differentiation method of the invention.

Preferably, said control neuronal phenotype is the neuronal phenotype of a population of neuronal-like cells of one or more subject(s) affected by a neurological disorder, which is obtainable according to the in vitro differentiation method of the invention.

Preferably, the above method is used for in vitro diagnosis of a neurological disorder, more preferably of a neuropsychiatric disorder such as schizophrenia.

In another aspect of the present invention, the population of neuronal-like cells according to the invention may be used to determine whether a patient will respond or not to therapy, such as a therapy performed with a compound identified according to the screening method above.

The population of neuronal-like cells according to the invention may indeed be useful to elucidate new opportunities for treatment in non-responding patients or indicate one treatment over other treatment choices. For example, pre-selecting patients who are more likely to respond well to an agent or combination of agents can reduce the number of patients needed in a clinical study or accelerate the time needed to complete a clinical development program.

Therefore, the present invention further provides herein an in vitro method for determining a neurological disorder drug-responding or non-responding phenotype comprising the steps of:
a) obtaining a population of neuronal-like cells of a subject suffering from a neurological disorder according to the in vitro differentiation method described above;
b) comparing the neuronal phenotype of the population of neuronal-like cells of said subject to one or more control neuronal phenotype(s); and
c) determining the neurological disorder drug-responding or non-responding phenotype from said comparison.

According to the present invention, a "neurological disorder drug-responding phenotype" refers to a response state of a subject to the administration of neurological disorder drug. A "response state" means that said subject responds to the treatment, i.e. that the treatment is efficacious in said subject. A responding phenotype is thus characterized by an improvement in clinical symptoms, i.e. in the context of the present invention, an neurological disorder drug-responding phenotype is characterized by a regression or disappearance of any signs or symptoms of said neurological disorder. By contrast, a "neurological disorder drug-non responding phenotype" refers to the absence in said subject of a state response, meaning that said subject is refractory to the treatment.

Preferably, the control neuronal phenotype used in the above method is the neuronal phenotype of a population of functional neuronal-like cells of one or more healthy subject(s), which is obtainable according to the in vitro differentiation method of the invention.

Preferably, said control neuronal phenotype is the neuronal phenotype of a population of neuronal-like cells of one or more subject(s) affected by a neurological disorder, which is obtainable according to the in vitro differentiation method of the invention.

Still, preferably, the control neuronal phenotype used in the above method is the neuronal phenotype of a population of functional neuronal-like cells of one or more non-responding patients, which is obtainable according to the in vitro differentiation method of the invention.

In order to diagnose or prognose a neurological disorder, or to determine a neurological disorder drug-responding or non-responding phenotype as described above, it can be useful to provide a kit comprising one or more control populations of neuronal-like cells obtainable according to the in vitro differentiation method described above.

It is thus another aspect of the present invention to provide a kit for use in any method described above, comprising one or more control populations of neuronal-like cells obtainable according to the in vitro differentiation method described above, optionally bound to a solid support as described above.

Preferably, said kit further comprises instructions for its use in a method of the invention. As used herein, the term "instructions" refers to a publication, a recording, a diagram, or any other medium of expression which can be used to communicate how to perform a method of the invention. Said instructions can, for example, be affixed to a container which contains said kit.

Preferably, the control population of neuronal-like cells used in the above kit is a population of functional neuronal-like cells of one or more healthy subject(s).

Preferably, said control population of neuronal-like cells is a population of neuronal-like cells of one or more subject(s) affected by a neurological disorder.

According to another preferred embodiment, said kit comprises one or more control populations of neuronal-like cells directly obtained according to the in vitro differentiation method described above, optionally bound to a solid support.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

Figure 1:
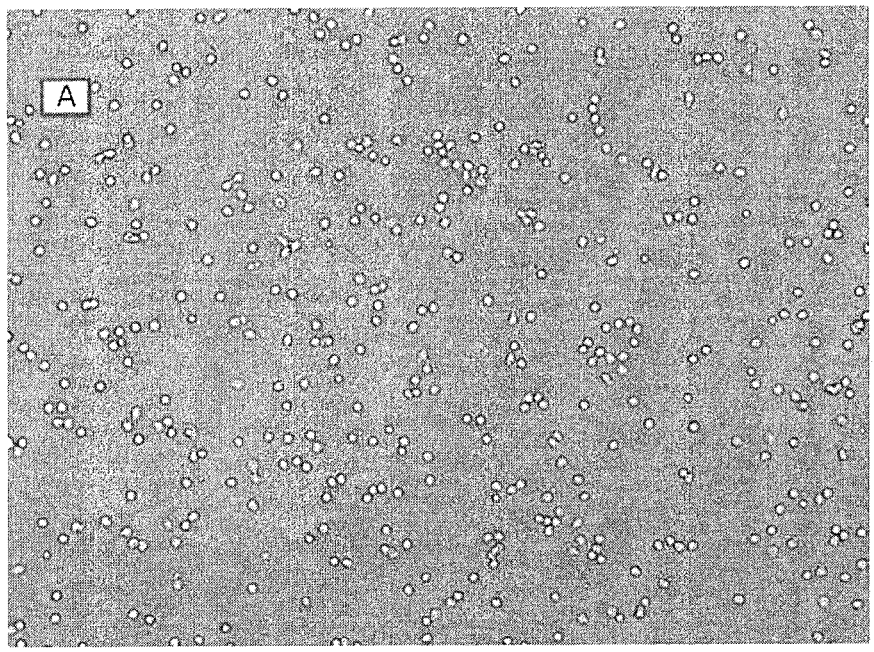
FIG. 1. Monocytes 15 minutes after plating, shown with light microscopy (A) at a 10× magnification and (B) at a 20× magnification.
Figure 1:
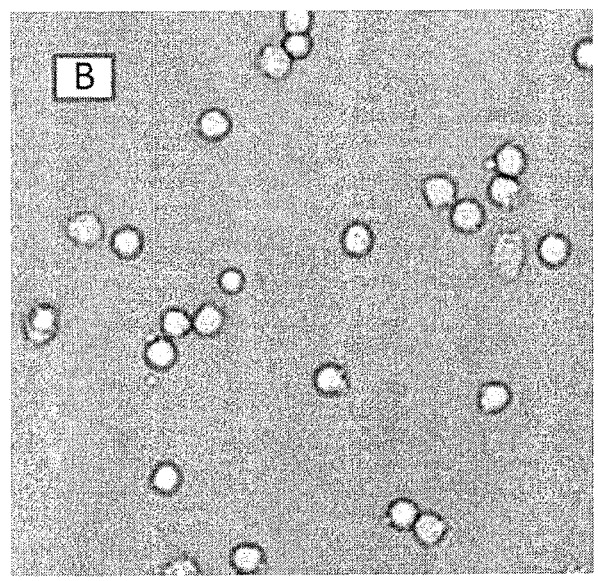

(A) FACS diagrams and microscopy photographs from cells treated according to the protocol of the invention. Cells were analyzed at days 4, 7, 10, and 20, respectively. At day 20, a high proportion of the cells were differentiated into a neuronal phenotype (see microscopy photograph—the arrows indicate some of the cells differentiated into neuronal-like cells), which were no longer positive for CD14 or CD34 (see FIG. 2D for CD14 expression in neuronal-like cells at day 20).

(B) Western-blot performed on samples from 5 subjects showing the presence of CD34 at day 7 and 10. A statistically significant increase of CD34 expression was observed between the monocytes stage and the pluripotential macrophages stage (days 7 and 10). Protein loading was controlled with amidoblack staining; no differences were observed between loading samples (right diagram).

(C) CD14 expression in macrophages maintained under standard culture conditions versus functional neuronal-like cells from the same individual at day 20 (13 subjected tested). A significant decrease in CD14 expression was observed in neuronal-like cells.

(D) Immunofluorescence staining showed that neuronal-like cells (rounded somas and long thin neurites) no longer express CD14, while other cells remained positive for this marker.

Figure 3:
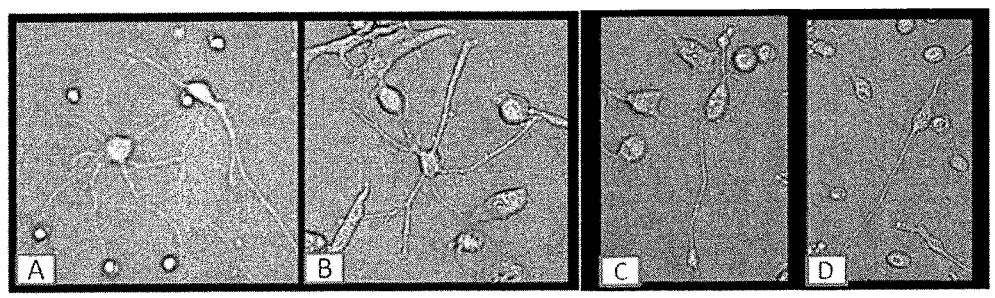

FIG. 3. Light microscopy of (A) human neurons after 7 days in culture, and (B), (C) and (D) of macrophage-derived-neuronal-like cells (MDNs) produced according to the method of the invention at day 20.

Figure 4A:
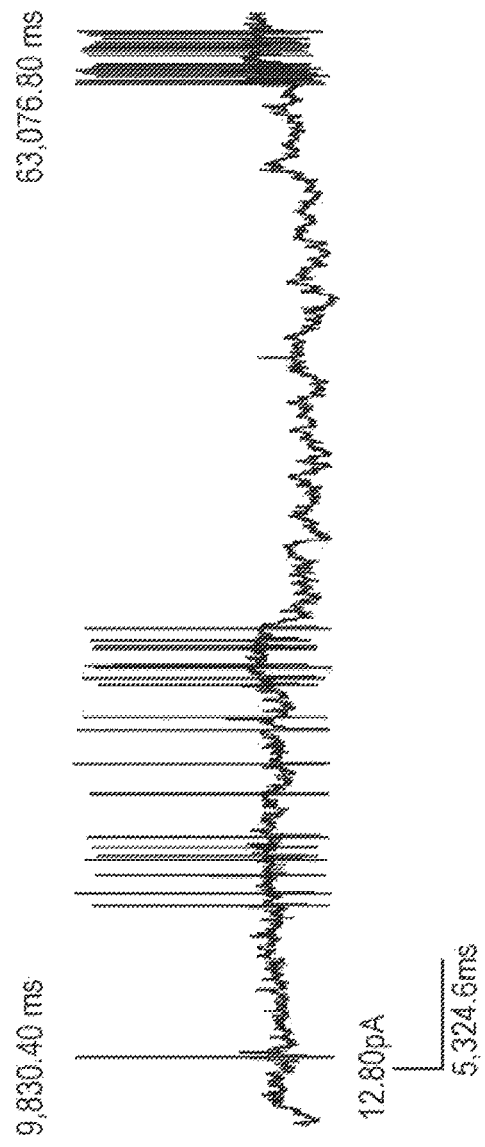
Figure 4C:
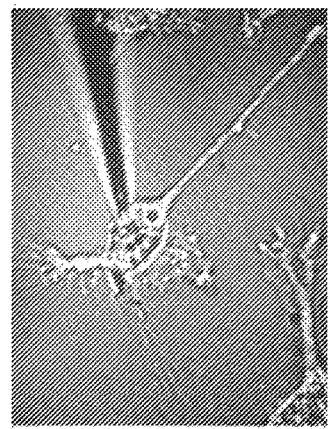
Figure 4B:
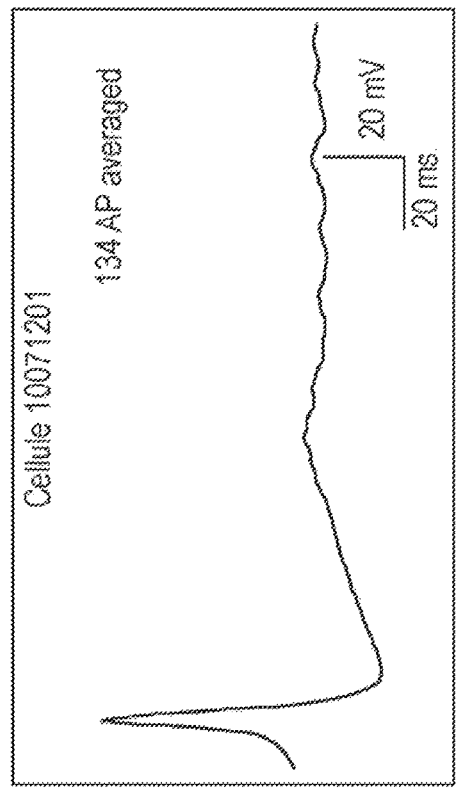

FIG. 4. Electrophysiological recordings of MDNs action potentials.

(A) Spontaneous action potentials recorded from MDNs under current clamp conditions.

(B) 134 averaged action potentials.

(C) Representative cell from which recordings were made.

Figure 5A:
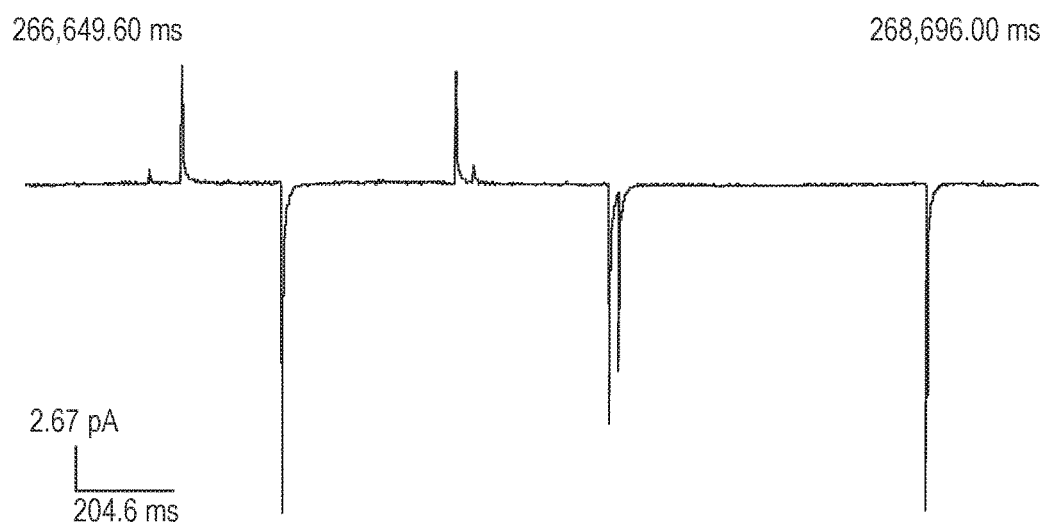
Figure 5B:
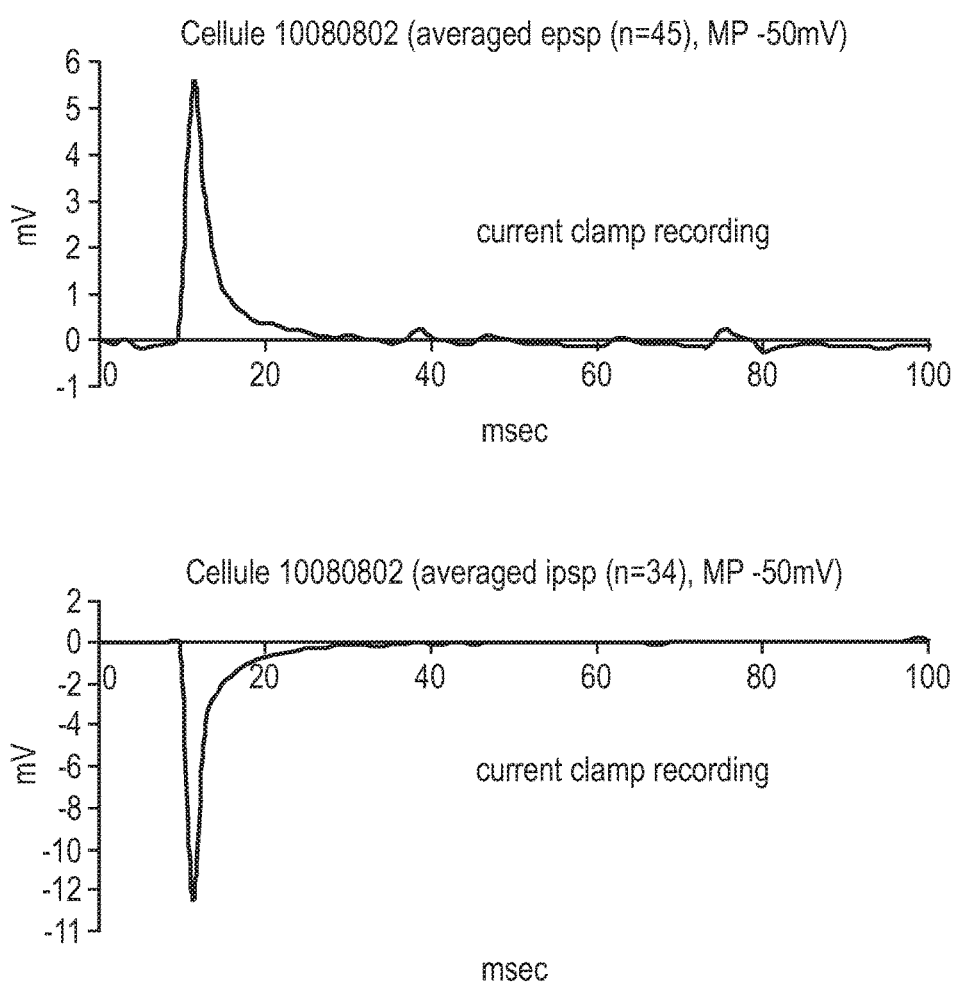
Figure 5C:
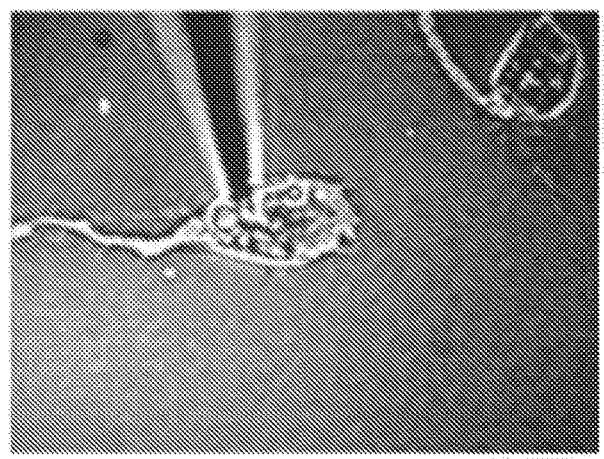

FIG. 5. Electrophysiological recordings of MDNs post-synaptic potentials.

(A) Spontaneous excitatory postsynaptic potentials (EPSPs) and inhibitory postsynaptic potentials (IPSPs) recorded from MDNs under current clamp conditions.

(B) 45 averaged EPSPs and 34 averaged IPSPs. Recordings were obtained from 11 cells from 5 different individuals.

(C) Representative cell from which recordings were made.

Figure 6A:
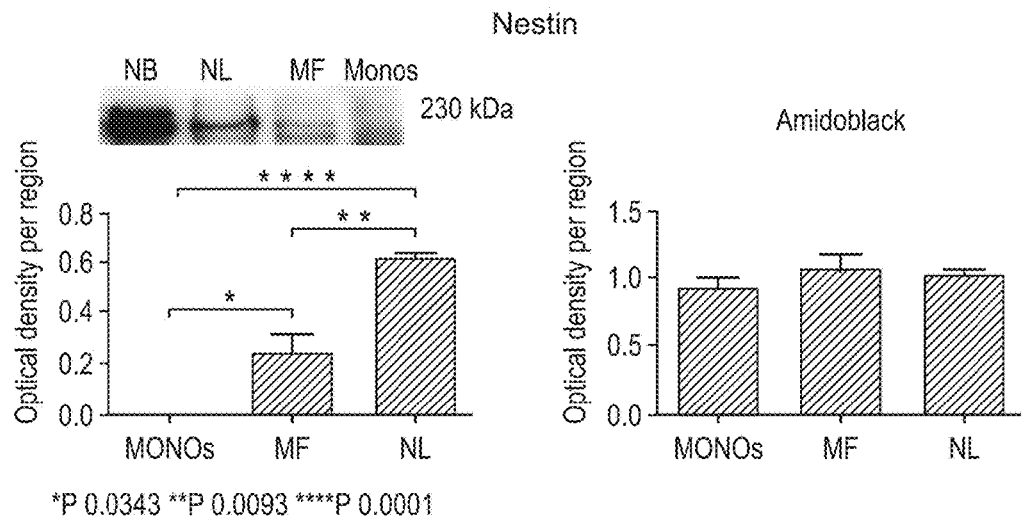
Figure 6B:
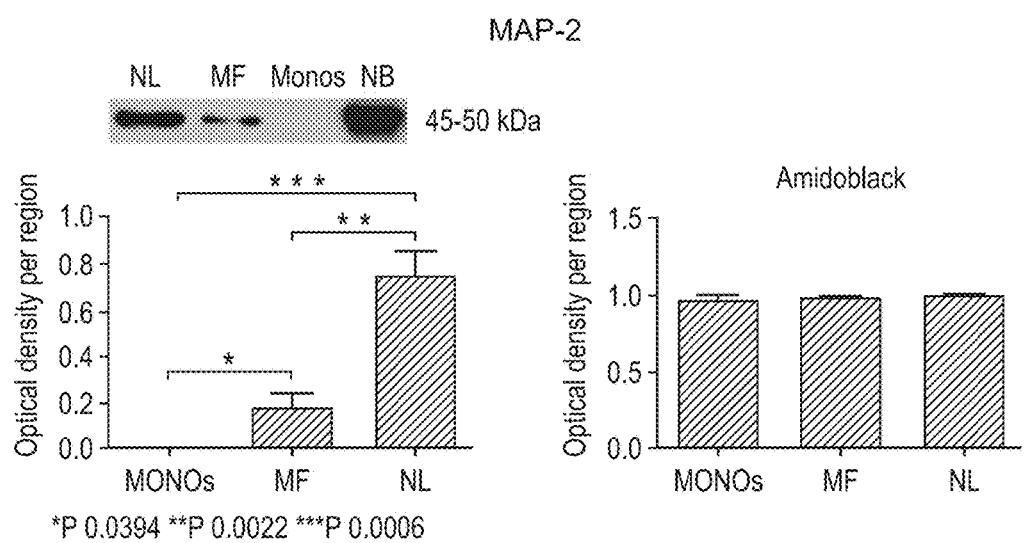
Figure 6C:
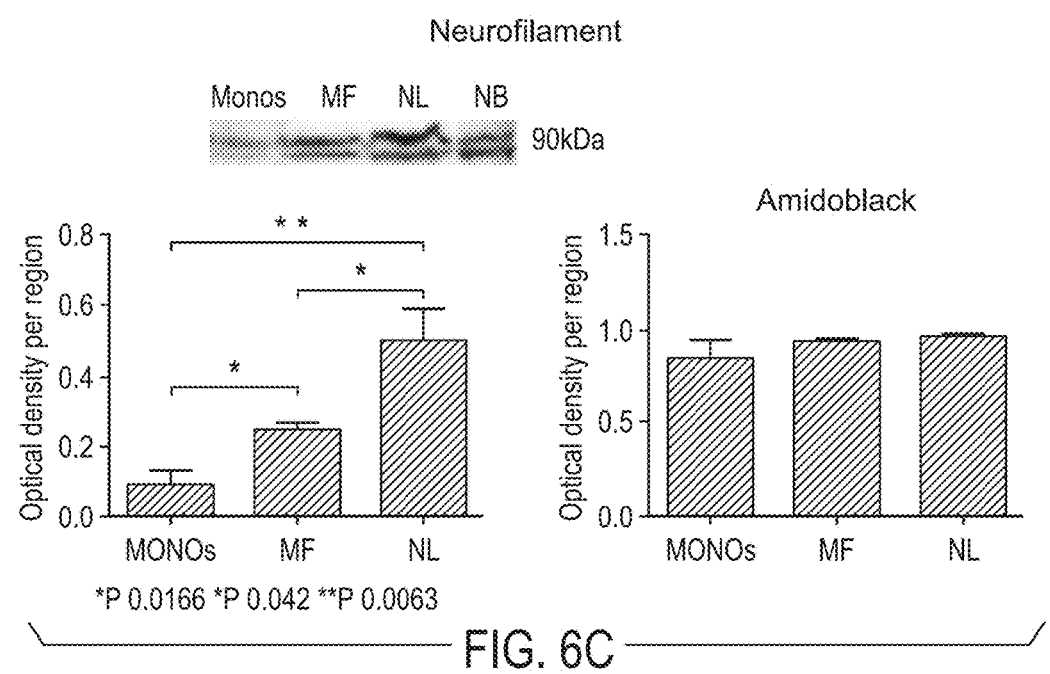

FIG. 6. Western Blots measuring optical density per region analysis of neuronal markers such as Nestin (A), MAP-2 (B) and Neurofilament (C).

A statistically significant increase in expression of those neuronal markers was observed between monocytes and pluripotent macrophages. This increase became more prominent in differentiated neuronal-like cells. Protein loading was controlled with amidoblack staining; no differences were observed between loading samples (right diagram). Protein extracts were obtained from 3 to 5 different subjects. Between 4 to 5 different Western Blots were included for this statistical analysis.

NB=neuroblastoma cells (positive control), NL=neuronal-like cells, MF=pluripotential macrophages, Monos=monocytes.

Figure 7:
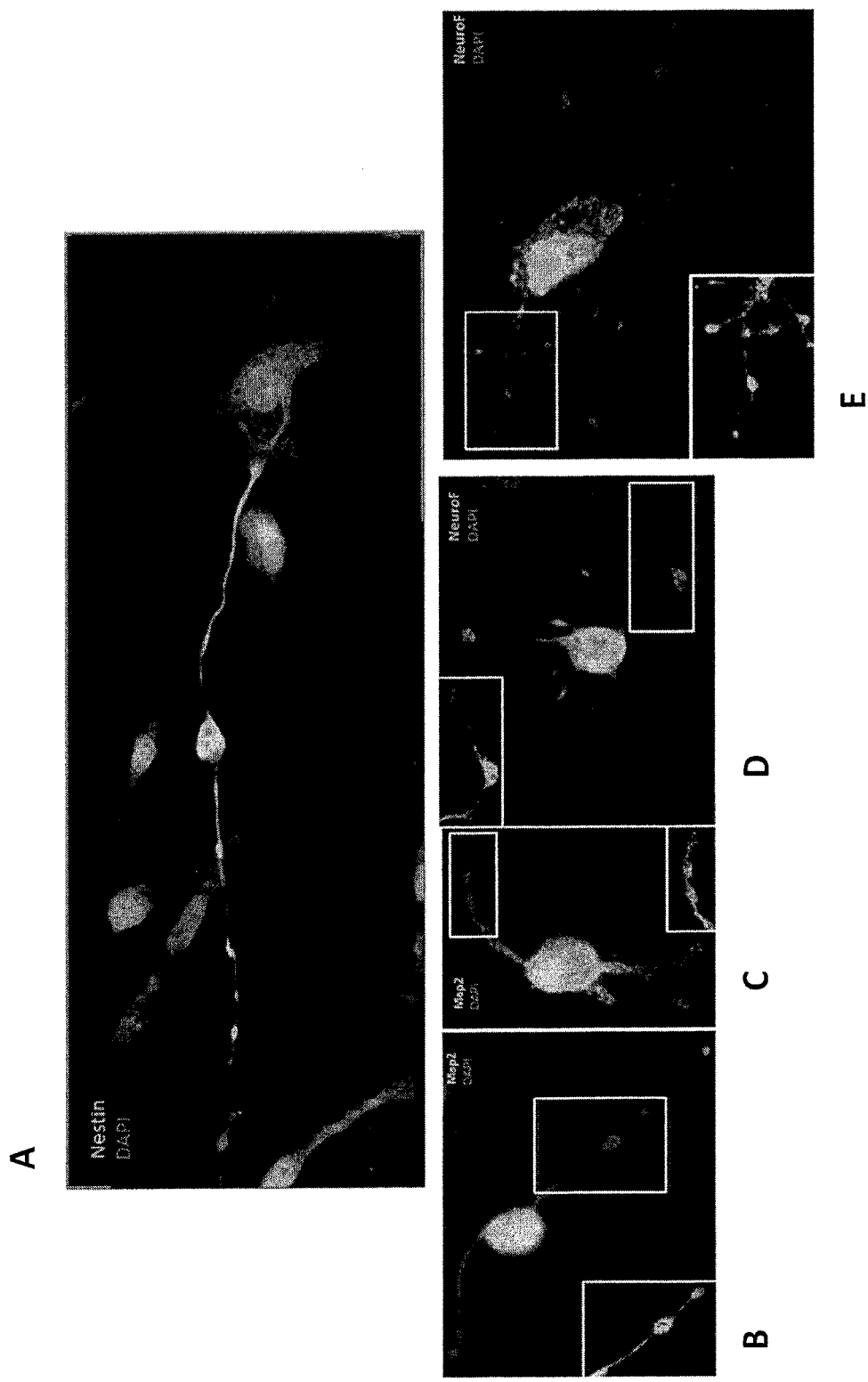

FIG. 7. Immunofluorescence stainings showing the localization of neuronal markers such as Nestin (A), MAP-2 (B,C) and Neurofilament (D,E), and of the nucleus (DAPI).

Figure 8A:
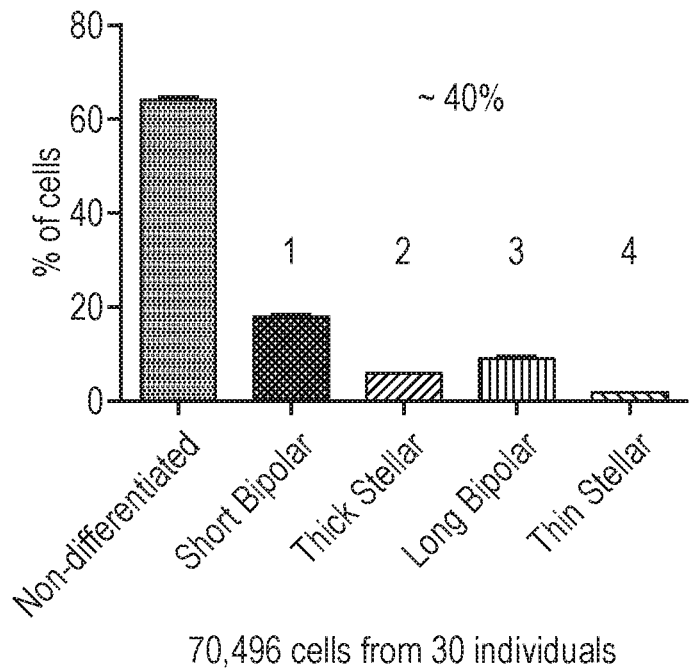
Figure 8B:
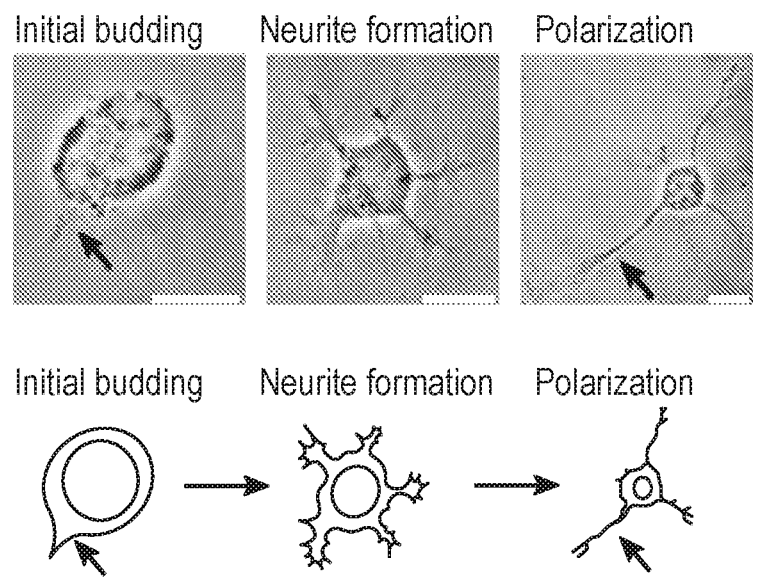
Figure 8C:
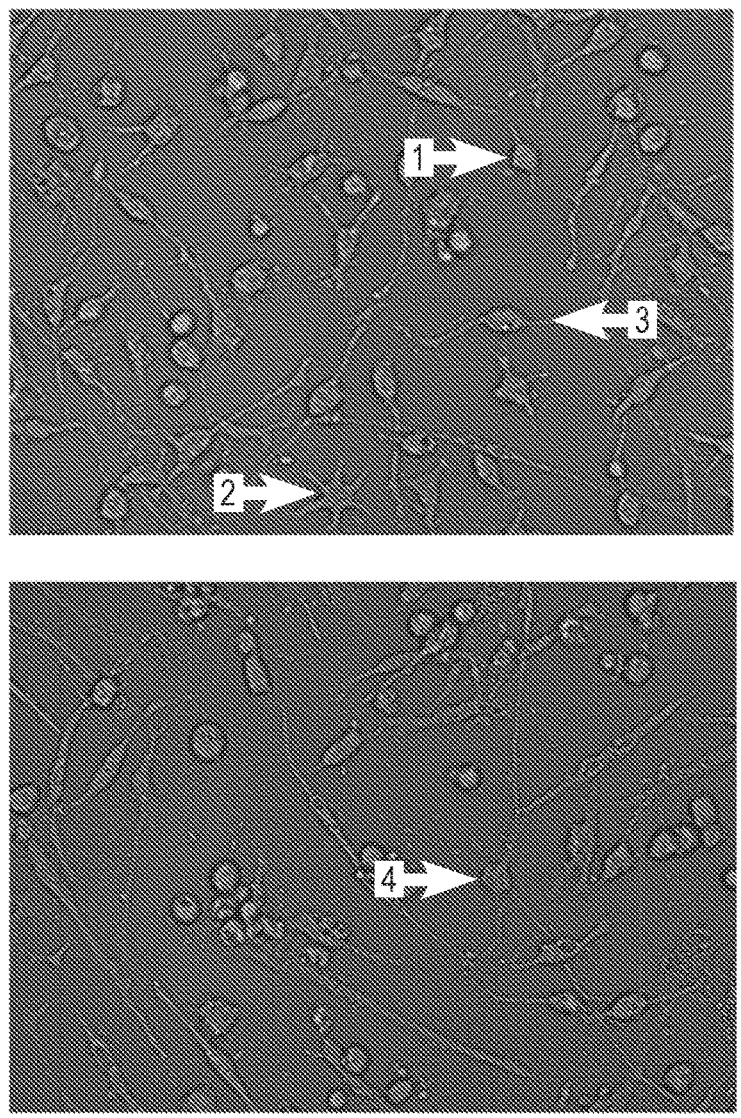

FIG. 8. Differentiation rates.

(A) Percentage of differentiated cells (approximately 40%). 70,496 cells were counted from 30 individuals.

(B) Differentiated cells were divided according to the shape they acquired during the differentiation process according to the classification established by Da Silva et al. (2002).

(C) Microscopy photographs showing different shapes of Macrophage-Derived-Neuronal-like cells (MDNs) including short bipolar cells (1), thick stellar cells (2), long bipolar cells (3) and thin stellar cells (4).

Figure 9:
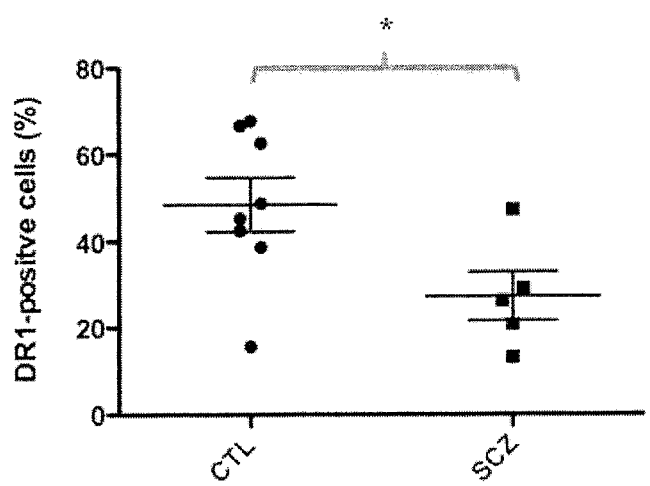

FIG. 9. Expression of Dopamine 1 Receptor (DR1) in MDNs from 5 patients affected by schizophrenia and from 8 healthy control individuals. DR1 expression was measured via FACS.

Figure 10A:
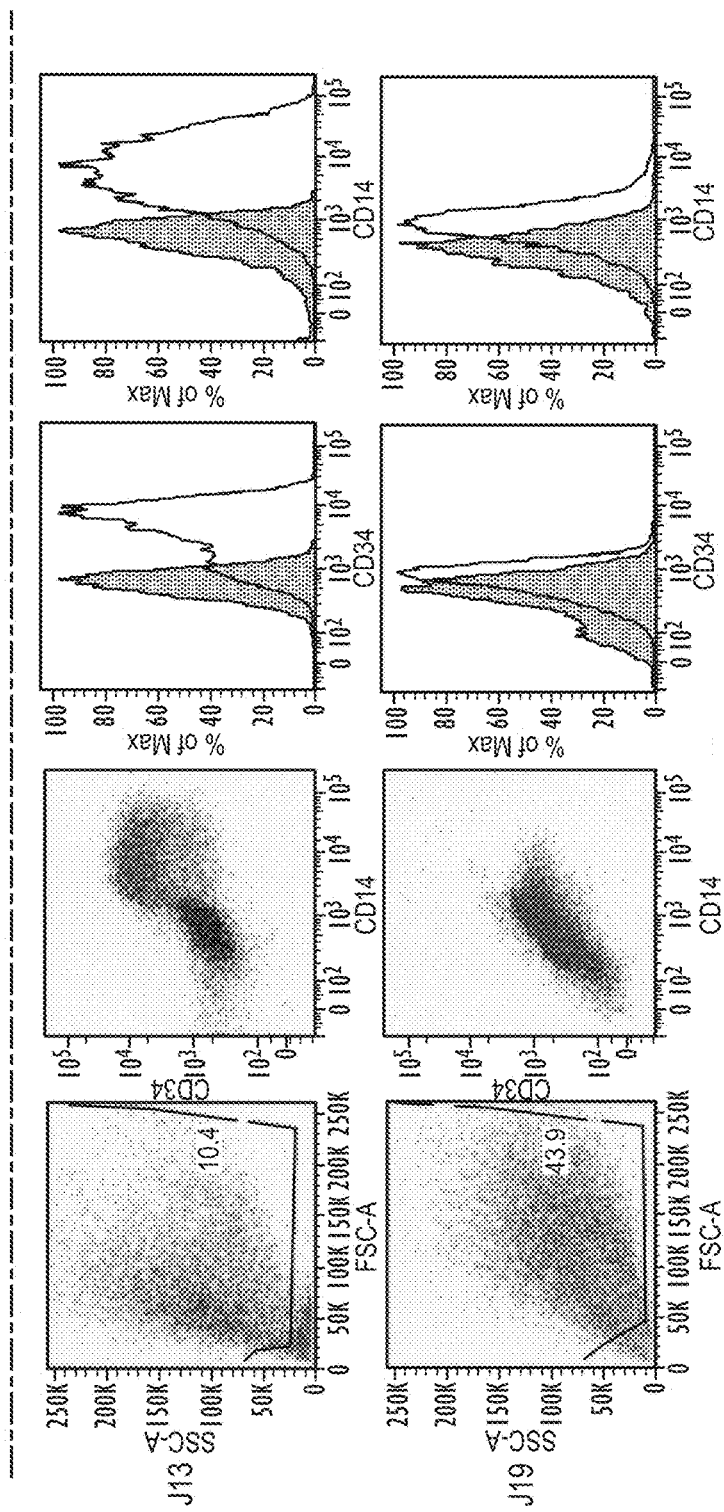
Figure 10B:
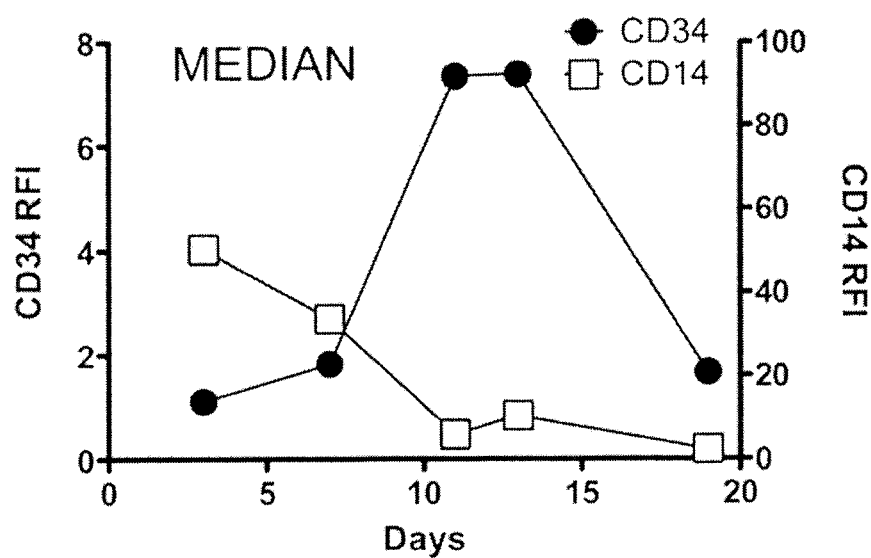
Figure 10C:
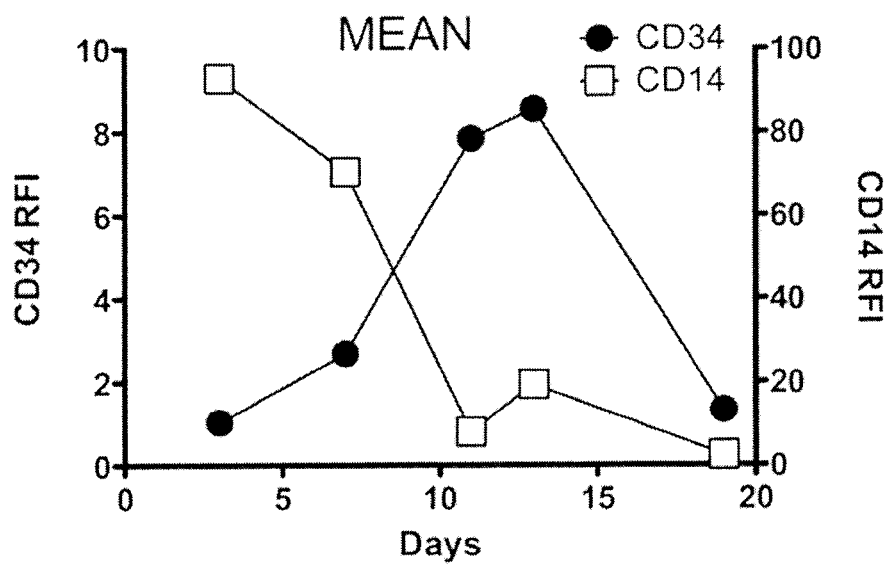

FIG. 10. (A) Representative FACS experiment from one individual showing differential expression of CD14 and CD34 during days 4, 7, 11, 13 and 19. (B) Median CD34 and CD14 RFI. (C) Mean CD34 and CD14 RFI (RFI: Relative Fluorescence Intensity).

EXAMPLES

1. Material and Methods 1.1. Material required
1. Fibronectin human from plasma (Sigma-Aldrich ref. F2006)
2. DMEM-Dulbecco's Modified Eagle Medium, High Glucos (GutaMAX™ from GIBCO catalog #61965059)
3. Foetal Bovine Serum (FBS), 500 ml (GIBCO (Invitrogen), Lot. 41G8072K, ref. 10270-106 or ref. 10270-106, lot. 41 G6298P)
4. Stericup Millipore filtration unit with a 0.22 µm pore, PES (catalogue # SCGPU05RE)
5. NaCl/Sodium chloride 0.9% sterile solution 1000 ml (Baxter ref # UKF7124)
6. Human Neurotrophin-3 (NT-3) (Peprotech ref #450-03-100)
7. Butylated hydroxyanisole (BHA) (Sigma-Aldrich, product # B1253-100G, CAS #25013-16-5Re)
8. Retinoic Acid (RA) (Sigma-Aldrich ref # R2625)
9. Recombinant human Insulin Growth Factor-1 (IGF-1) (Peprotech, catalog #100-11)
10. Potassium chloride (KCL) (Sigma-Aldrich ref # P5405)
11. Human recombinant macrophage colony stimulating factor (MCSF) (Abcys, catalogue #300-25)
12. PBS Dulbecco's w/o CA MG (1×) 10×500 ml (Invitrogen, Ref #141-901-69)
13. Ultra-pure DNAse/RNAse-free distilled water, 10×500 ml (Invitrogen, Ref #10977049)
14. Sterile Falcon tubes 50 ml polypropylene (BD, ref #352070, 50 ml high-clarity polypropylene conical centrifuge tube, sterile 25/sp, 500/ca)
15. 6 well plastic plates (BD Falcon ref #351146)
16. 12 well plastic plates (BD Falcon ref. #353043)
17. 25 cm2 flasks (70 ml) (BD Falcon ref #353109)
18. EDTA buffer, pH 8, 0.5M, 4×100 ml (Invitrogen, ref #15575020)
19. Ficoll-paque plus, endotoxin tested, (<0.12 EU/ml) density 1.077±0.001 g/ml 500 ml (GE Healthcare catalogue #17-1440-03, lot 10038368)
20. Trypan Blue Solution 0.4% (GIBCO)
21. CD14 human Microbead (Miltenyi Biotec ref #130-050-201)
22. MACS Magnetic separator and Multi stand (Miltenyi Biotec 130-042-303)
23. MS columns from MACS (Miltenyi Biotec 130-041-301)

1.2. Methods 1.2.1. Preparation of Culture Plates, Buffers and Culture Medium i. Preparation of MACS Buffer MACS buffer was prepared with sterile PBS pH 7.2 supplemented with 5% Fetal Bovine Serum (FBS) and 2 mM EDTA, and subsequently filtered MACS buffer was maintained at 4° C. while carrying out the method of the invention, as indicated further below.

ii. Coating of Culture Plates with Fibronectin 6-well and 12-well plastic plates were coated with 20 µg/ml human fibronectin from plasma (Sigma-Aldrich), according to the following procedure.

The 20 µg/ml fibronectin solution was directly added to plastic plates and flasks, without any prior washing: 1.5 ml and 0.75 ml of 20 µg/ml fibronectin were added to each single well of 6- and 12-well plates, respectively, and 4.5 ml of 20 µg/ml fibronectin was added to 25 cm² falcon flasks. The coated items were then immediately placed at 4° C.

The fibronectin solution was left in plastic plates and flasks at 4° C. for 12 to 17 hours. After coating, the remaining fibronectin solution was removed and discarded, and 2 washes were performed with sterile PBS 1× at 4° C. The plastic plates and flasks were then stored at 4° C. with sufficient volume of PBS 1× to prevent any drying. Plastic plates and flasks coated according to the above procedure could be stored at 4° C. for up to a month as long as they did not dry out.

iii. Preparation of Culture Medium

The culture medium used according the present method was DMEM High Glucose, GutaMAX™ (GIBCO), supplemented with 10% Fetal Bovine Serum (FBS), which was prepared according to the following procedure.

50 ml of defrosted FBS was added to a 500 ml GutaMAX™ bottle. The DMEM supplemented with 10% FBS was then filtered with a stericup Millipore filtration unit PES 0.22 µm. No decomplementation protocols were followed to treat FBS.

DMEM before and after FBS supplementation was maintained at 4° C.

1.2.2. Blood Preparation

Fresh blood samples collected from 40 different subjects were used to carry out the method according to the invention, and was processed within 24 hrs of collection at room temperature, in order to avoid affecting cell viability. The shortest the period of time between blood collection and gradient separation of blood components, the better.

i. Separation of Blood Components by Ficoll Gradient to Collect White Blood Cells 3 different types of blood collection from 40 individuals were tested and all provided comparable differentiation results:

(1) blood collected in either 5 ml or 10 ml EDTA purple tubes;
(2) blood collected in a 400 ml bag of freshly donated blood;
(3) blood collected in filters known as "cones", which are used to separate blood cells from plasma and serum, and contain small volumes of highly concentrated blood (such as 5-7 ml), i.e. a very high number of blood cells. The gradient separation of blood within these cones was slightly different as indicated further below.

At least 30 to 40 ml of whole non-concentrated blood (from blood collection (1) or (2)) was needed to replicate the exact conditions of the present protocol. Indeed, this specific volume allows the obtention of about 6 to 12 wells of differentiated cells, i.e. of about 500 000 to 1 million differentiated cells based on a differentiation rate of 20%.

PBMC were separated by Ficoll gradient according to the procedure described by Fuss et al. (2009).

After recovering the white blood cells via a Ficoll gradient and washing said cells in sterile saline solution, 40 ml of sterile saline solution was added to the pellet containing the white blood cells, which were homogenized by using a 10 ml pipette and a pipette boy for about 5 to 10 passages (by pulling and extracting the liquid). Should the cells not be completely homogenized after 10 passages, a second wash was performed according to the same procedure; pipetting was not recommended to avoid damaging the cells.

Once the cells were homogenized, the tubes were further centrifuged at 1200 RPM for 10 min at 4° C. to initiate a gradual change of temperature to the cells, and the supernatant discarded. Pellets were pulled into one 50 ml falcon tube, to which 40 ml of MACS buffer at 4° C. was added to prevent any cell clotting, and the white blood cells were then again homogenized with the use of a pipette and a pipette boy (for about 5 passages).

ii. Culture of PBMCs and Magnetic Isolation of Monocytes (CD14+ Cells)

Viability of the white blood cells was then assessed via the Trypan Blue method.

About 13.5 millions of viable PBMCs (Peripheral blood mononuclear cells) were centrifuged and resuspended into 10 ml of DMEM/10% FBS at 4° C. The PBMCs cells were then slowly plated into a 25 cm² flask pre-coated with fibronectin at 4° C. as described above, the flask being positioned horizontally, so as to allow an even distribution of the cells throughout the surface. The flask was then incubated at 37° C. with 5% $CO_2$.

The remaining viable PBMCs were used for magnetic isolation of CD14+ cells (i.e. monocytes), which usually account for 15 to 20% of PBMCs, based on the manufacturer protocol (Miltenyi).

1.2.3. Differentiation of Monocytes Isolated from PBMC into Pluripotent Macrophages Monocytes were subsequently cultured and differentiated according to the following protocol.

Day 0

Isolated monocytes were centrifuged and resuspended in DMEM/10% FBS at a concentration of 550 cells/ml. M-CSF (Macrophage colony-stimulating factor) was added to resuspended cells at a concentration of 1:2000 with a stock solution at 0.1 mg/ml.

1.2 million monocytes were plated per each 9.6 cm² well of a 6-well plate, 550,000 monocytes per each 3.1 cm² well of a 12-well plate, and 6 million monocytes per each 25 cm² flask. To ensure that monocytes became confluent and evenly distributed, and thus maintained a good differentiation rate, flasks and plates remained horizontal throughout the protocol, plating was done slowly by gently releasing monocytes from the pipette. Plated cells were left at room temperature for at least 15 min so that cells became fully attached to the surface of the plates or flasks, and subsequently incubated at 37° C. with 5% $CO_2$ until day 4.

Day 4

To collect the conditioned medium of the PBMCs at day 4, the following steps were carried out:
a) pre-heating 10 ml of DMEM/10% FBS in an incubator bath at 37° C. for about 20 min;
b) collecting the PBMCs conditioned medium from the 25 cm² PBMCs flask corresponding to a subject in a 15 ml polypropylene falcon tube;
c) adding the pre-heated 10 ml of DMEM/10% FBS to the flask, and incubate the flask again at 37° C. with 5% $CO_2$;
d) centrifugating the PBMCs conditioned medium collected at step b) at 1200 RPM for 7 min at room temperature;
e) in the meantime, heating another 10 ml of DMEM/10% FBS in a different 15 ml polypropylene falcon tube at 37° C. for about 20 min;
f) heating the PBMCs conditioned medium of step d) at 37° C. for about 7 min, without disrupting the pellet or mixing it again with the conditioned medium.

Once the tubes of steps e) and f) were at 37° C., monocytes treatment could be started as follows:
g) discarding the medium of the 6- and 12-well plates containing the monocytes isolated from the same subject as the PBMCs of step b);
h) adding the DMEM and the conditioned medium to each well of the plates in a 2:1 ratio, i.e.:
  2 ml of DMEM/10% FBS of step e) and 1 ml of PBMCs conditioned medium of step f), for each well of a 6-well plate, and
  666 µl of DMEM/10% FBS of step e) and 333 µl of the PBMCs conditioned medium of step f), for each well of a 12-well plate;
i) incubating the plates at 37° C. with 5% $CO_2$ until day 7.

At day 4, no growth factors or antioxidants are added to the culture medium of the monocytes.

1.2.4. Differentiation of Pluripotent Macrophages into Neuronal-Like Cells

Day 7

Steps a) to f) as described above were carried out to collect the conditioned medium of the PBMCs at day 7.

Once the tubes of steps e) and f) were at 37° C., the growth factor BHA (butylated hydroxyanizole) was added to the culture medium of monocytes at a final concentration of 50 nM, as follows:
g) adding 10 µl of 100 mM BHA (0.0089 grams of BHA+500 µL ethanol) to the 10 ml of DMEM/10% FBS of step e), thereby obtaining a 100 µM BHA/DMEM solution. Then diluting 10 µl of this 100 µM solution with a further 10 ml of DMEM/10% FBS heated at 37° C., thereby obtaining a 100 nM BHA/DMEM solution;
h) discarding the medium of the 6- and 12-well plates containing the monocytes isolated from the same subject as the PBMCs of step b);
i) adding the BHA/DMEM solution and the conditioned medium to each well of the plates in a 1:1 ratio, i.e.:
  1.5 ml of the 100 nM BHA/DMEM of step g) and 1.5 ml of the PBMCs conditioned medium of step f), for each well of a 6-well plate, and
  1 ml of the 100 nM BHA/DMEM of step g) and 1 ml of the PBMCs conditioned medium of step f), for each well of a 12-well plate;
j) incubating the plates at 37° C. with 5% $CO_2$ until day 10.

Day 10

Steps a) to f) as described above were carried out to collect the conditioned medium of the PBMCs at day 10.

Once the tubes of steps e) and f) were at 37° C., the growth factor BHA (butylated hydroxyanizole) and the antioxidant Retinoic Acid (RA) were added to the culture medium of monocytes at a final concentration of 50 nM and 16 μM, respectively, and by maintaining the temperature at 37° C., as follows:

g) preparing a 100 nM BHA/DMEM solution as described above for day 7;
h) adding 20 μl of 16 mM RA (0.0016 grams of RA+3.32 ml ethanol) to the 10 ml of 100 nM BHA/DMEM solution of step e), thereby obtaining a 100 nM BHA/32 μM RA/DMEM solution;
i) discarding the medium of the 6- and 12-well plates containing the monocytes isolated from the same subject as the PBMCs of step b);
j) adding the supplemented DMEM of step h) and the conditioned medium to each well of the plates in a 1:1 ratio, i.e.:
   1.5 ml of the 100 nM BHA/32 μM RA/DMEM of step h) and 1.5 ml of the PBMCs conditioned medium of step f), for each well of a 6-well plate, and
   500 μL of the 100 nM BHA/32 μM RA/DMEM of step h) and 500 μl of the PBMCs conditioned medium of step f), for each well of a 12-well plate;
k) incubating the plates at 37° C. with 5% $CO_2$ until day 13.

Day 13

Steps a) to f) as described above were carried out to collect the conditioned medium of the PBMCs at day 13.

Once the tubes of steps e) and f) were at 37° C., IGF-1 (insulin growth factor-1), BHA (butylated hydroxyanizole), Retinoic Acid (RA), and Neurotrophin-3 (NT-3) were added to the culture medium of monocytes at a final concentration of 12.5 ng/ml, 50 μM, 16 μM, and 30 ng/mL, respectively, and by maintaining the temperature at 37° C., as follows:

g) preparing the IGF-1 solution before any of the other exogenous factors. First, mixing 2 μl of 0.5 mg/ml IGF-1 (1 mg of IGF-1+1 ml pure water+1 ml BSA 0.2%) with 4 ml DMEM/10% FBS of step e), so as to obtain a 0.25 μg/ml IGF-1/DMEM solution. Then diluting 1 ml of this 0.25 μg/ml solution with a further 9 ml of DMEM/10% FBS heated at 37° C., thereby obtaining a 25 ng/ml IGF-1/DMEM solution;
h) adding 5 μl of 200 mM BHA (0.0089 grams of BHA+250 μL ethanol) to the supplemented DMEM of step g), thereby reaching a 100 μM BHA concentration;
i) adding RA prepared as described on day 10 to the supplemented DMEM of step h);
j) adding 20 μl of 30 μg/ml of NT-3 (100 μg of human NT-3 from Peprotech+3 ml 0.1% BSA) to the supplemented DMEM of step i), thereby reaching a 60 ng/ml NT-3 concentration;
k) discarding the medium of the 6- and 12-well plates containing the monocytes isolated from the same subject as the PBMCs of step b);
l) adding the DMEM supplemented with IGF-1, BHA, RA and NT-3 of step g) and the conditioned medium to each well of the plates in a 1:1 ratio, i.e.:
   1.5 ml of the supplemented DMEM of step g) and 1.5 ml of the PBMCs conditioned medium of step f), for each well of a 6-well plate, and
   500 μL of the supplemented DMEM of step g) and 500 μl of the PBMCs conditioned medium of step f), for each well of a 12-well plate;
g) incubating the plates at 37° C. with 5% $CO_2$ until day 17.

Day 17

On day 17, no change of medium was performed, and only 25 mM of KCl was added to the monocytes medium. Alternatively, ionomycin could be used to replace KCl (e.g. 500 mg/ml ionomycin).

Briefly, 10 μl and 30 μl of a 2.5 mM KCl stock solution was added to each well of the 6- and 12-well plates, respectively. Plates were then further incubated at 37° C. with 5% $CO_2$ until day 20.

Days 20-25

By day 20, cells would be neuronal-like. After reaching this stage of differentiation cells would last for about 5 more days and then they start to detach. Any further experiment was conducted on neuronal-like cells between day 20 and day 22.

1.2.5. Measure of Hematopoietic and Neuronal Markers
   i. Measuring of Hematopoietic Markers
Flow Cytometric Analysis Cells differentiation was evaluated by immunofluorescence labeling with mAbs against CD14 (QDot 655-conjugated hybridoma clone TüK4, Invitrogen) and CD34 (phycoeythrin [PE]-conjugated hybridoma clone AC136, Miltenyi). Labeling was performed at 4° C. using PBS containing 5% fetal calf serum and 5 mM EDTA (Sigma). Cells were trypsinized, washed and incubated in labeling medium with human AB serum to block Fc receptors for 20 min. They were then labeled with conjugated antibodies for further 20 min. Events were acquired using a FACS BD LSR II flow cytometer and analyzed using Diva (BD Biosciences) followed by FlowJo (Version 8.7; TreeStar)
Western-Blot HUVEC and hCMEC/D3 cells were used as positive controls, as they both express CD34 (Lanza et al., 2001). Macrophages maintained under standard culture conditions were compared versus neuronal-like cells from the same individual to determine if the expression of CD14 actually decreased in neuronal-like cells. These experiments were ran from monocytes of 13 different subjects.

ii. Measuring of Neuronal Markers

Determination of the presence of neuronal markers was carried out by Western Blot (Optical density per region assessments) and by immunofluorescence (Grassi et al., 1998). Human neuroblastoma cells were used as positive control for neuronal markers.

The inventors controlled for potential loading errors by staining membranes with Amidoblack which has been described as a better method than using actin or tubulin when cells drastically modify their structure (Aldridge et al., 2008).

1.2.6. Electrophysiological Recordings of Neuronal-Like Cells

Current patch clamp conditions were used to determine the presence of electrical activity in these neuronal-like cells (see the protocol established by Feng et al., 2011). Over 200 electrophysiological recordings were obtained from 11 cells from 5 different individuals.

2. Results

2.1. Differentiation of Blood Circulating Monocytes into Pluripotent Macrophages (DAYS 0-10) Followed by Neuronal-Like Cells (DAYS 10-20)

At DAY 0, from the 30 ml of blood analyzed from each individual, monocytes isolation varied between 3.5 and 12 million. Monocytes were rounded cells that started to grow in size into pluripotent macrophages (FIG. 1). If not enough cells were plated at this early stage, the differentiation into neuronal-like cells would be affected. As shown in FIG. 2B, monocytes did not express CD34.

By DAY 4, cells were still rounded (FIG. 2A), and were positive for CD14, a marker for monocytes and macrophages. The cells did not express CD34, a marker of hematopoietic stem cells.

By DAY 7, cells started expressing CD34 and remained positive for CD14. Cells shape became fibroblastic; nonetheless, some cells were rounded.

By DAY 10, the differentiation process into neuronal-like cells was initiated as described above. Cells remained positive for both CD34 and CD14. Most cells became fibroblastic in shape. The expression of CD34 by pluripotent macrophages was confirmed by Western-blot performed on samples from 5 different subjects. A 55 kDa band specific for CD34 was encountered as shown in FIG. 2B (Lanza et al., 2001). Pluripotent macrophages expressed CD34 from DAY 7, which was maintained until at least DAY 10.

Figure 2A:
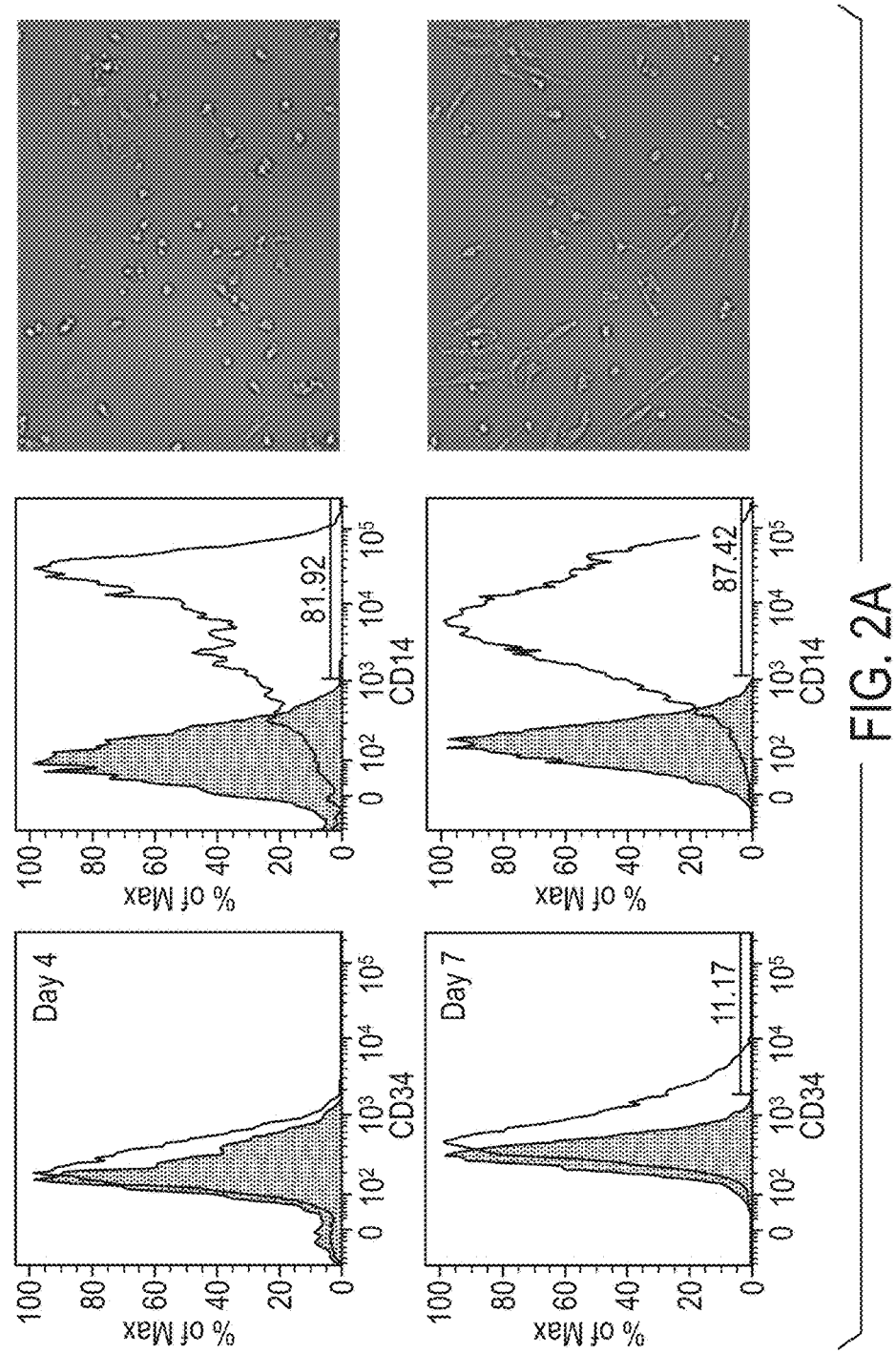
FIG. 2. Differentiation of blood circulating monocytes into pluripotent macrophages (Day 0 up to Day 7-10) and into functional neuronal-like cells (Day 7-10 up to Day 20).
Figure 2A:
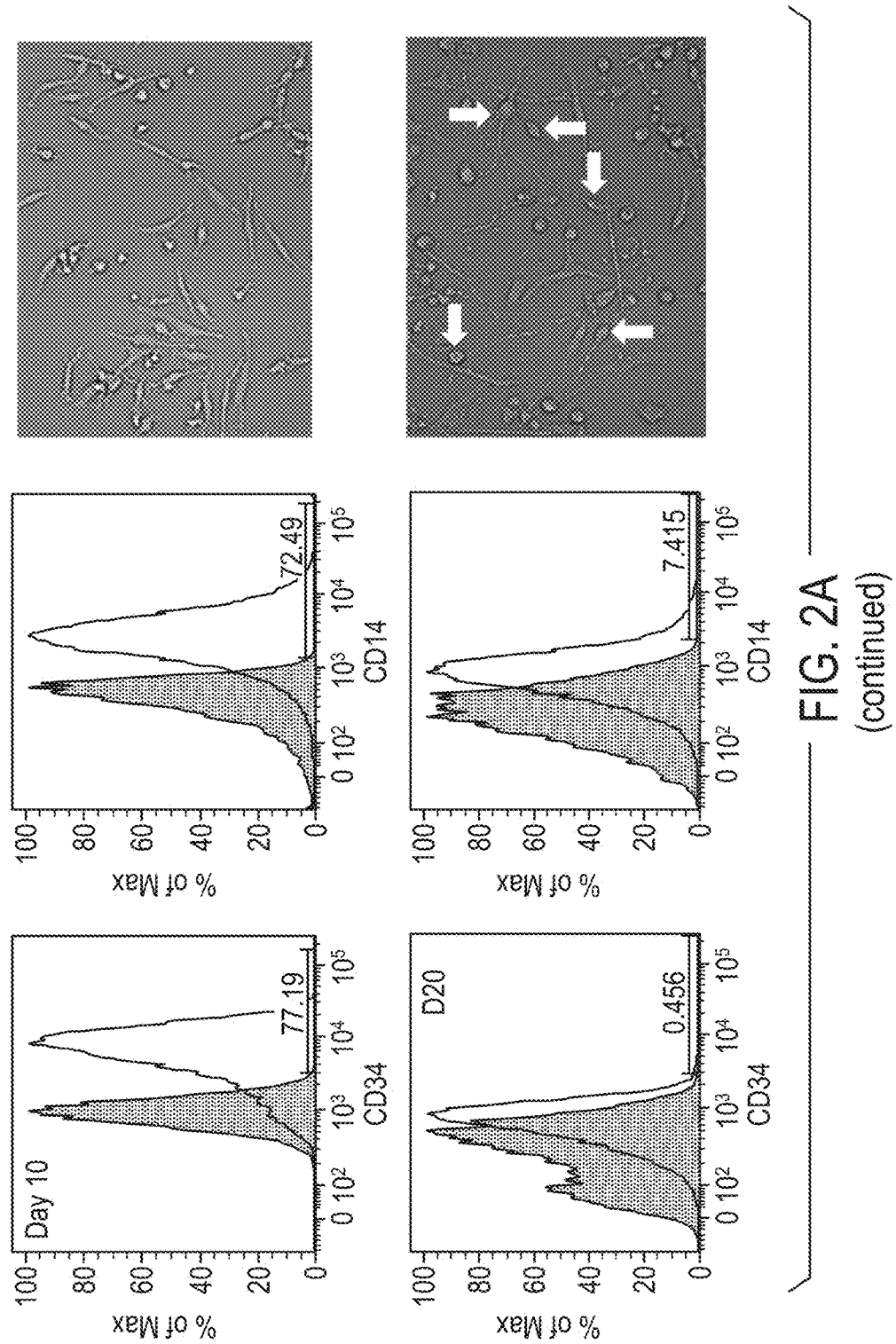
Figure 2B:
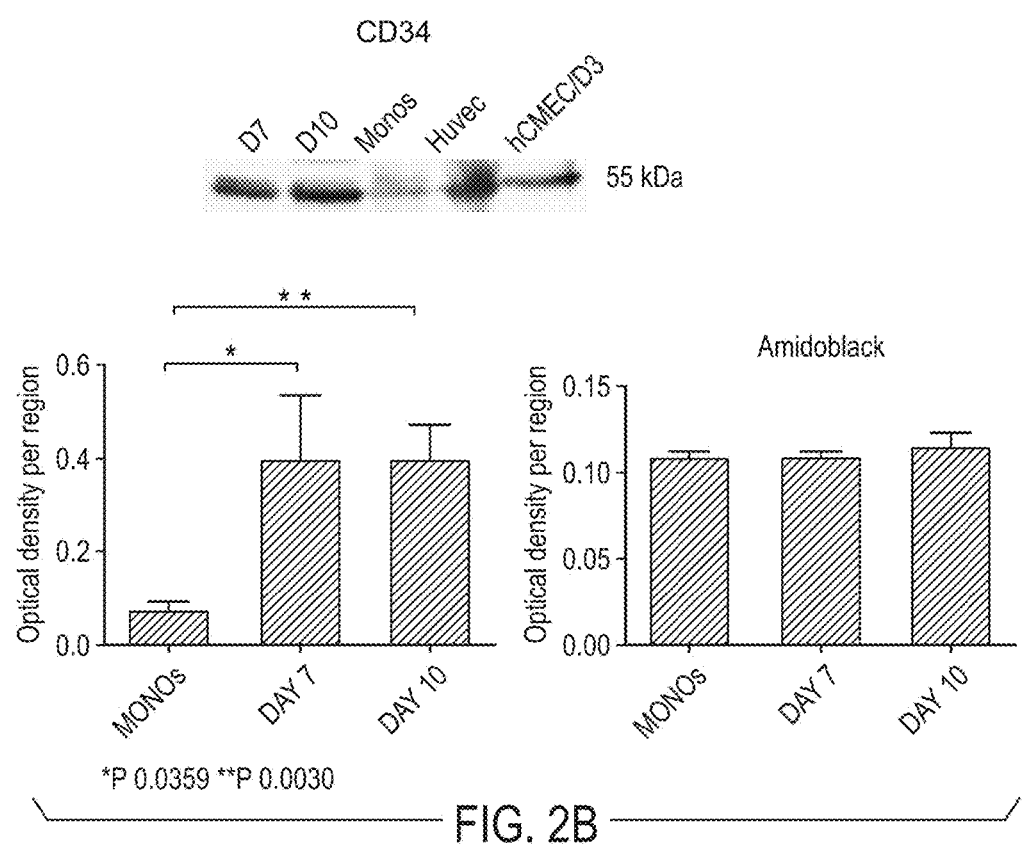
Figure 2C:
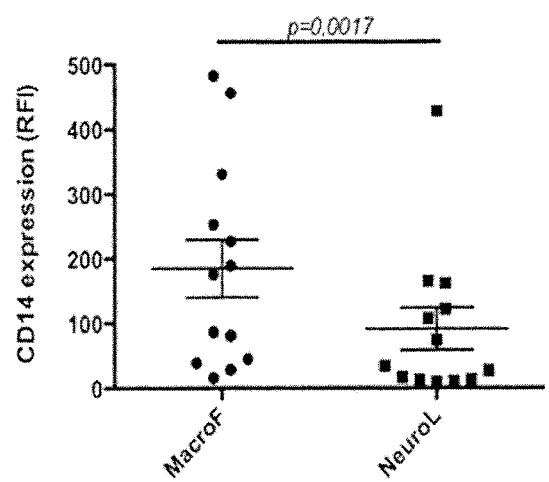
Figure 2D:
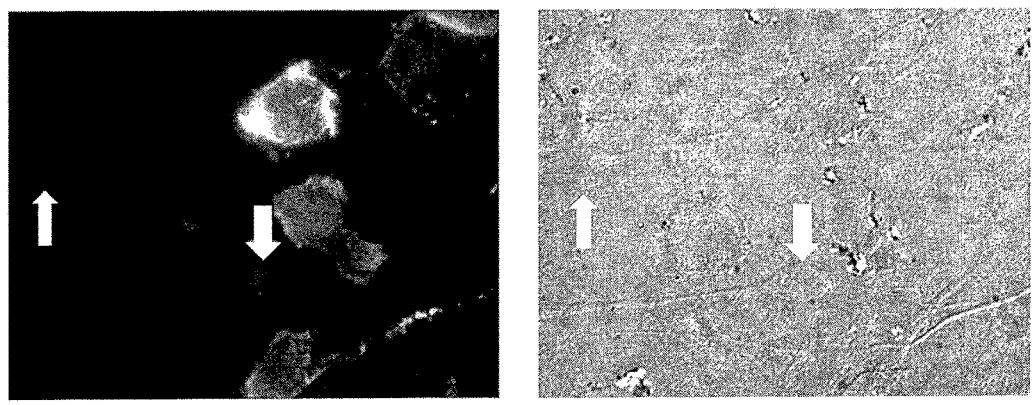

By DAY 20, expression of CD14 drastically decreased, and the cells were no longer positive for CD34 (FIGS. 2A and 2C). By immunofluorescence, it was identified that cells becoming negative for CD14 exhibited a neuronal phenotype with a rounded soma and thin long neuritis, and became either unipolar, bipolar or stellar (FIG. 2D). These neuronal-like cells obtained according to the method described herein and human neurons cultured for 5-7 days are structurally similar as shown in FIG. 3.

By contrast, decreasing the concentration of the exogenous factors diminished differentiation into neuronal-like cells, and increasing their concentration above the recommendations provided in the present application, or the number of doses, of at least BHA, RA and IGF-1, damaged the cells. Replacing IGF-1 by IGF-2 did not improve cell viability, while the use of FGF decreased the differentiation process.

2.2. Electrophysiological Recordings of Neuronal-Like Cells (MDNs)

Neuronal-like cells exhibited an electrical activity of a neuronal phenotype as presynaptic and postsynaptic electrical activity were detected (FIGS. 4 and 5). These cells were identified as macrophage-derived-neuronal-like cells (MDNs).

Spontaneous action potentials were recorded from MDNs under current clamp conditions (FIG. 4). In addition, spontaneous excitatory postsynaptic potentials (EPSPs) and inhibitory postsynaptic potentials (IPSPs) were recorded from MDNs under current clamp conditions (FIG. 5).

2.3. Expression of Neuronal Markers in Neuronal-Like Cells (MDNs)

Immunofluorescence assays showed that the neuronal markers Nestin, MAP-2 as well as Neurofilament were expressed in cells with neuronal phenotype (FIG. 7). The distribution of these neuronal markers coincide what is found in neurons. In particular, Nestin, Neurofilament and MAP-2 are present in the neuronal body as well as in neuronal extensions. These results were confirmed by Western Blot and Optical density per region assessments (FIG. 6). It showed as well that MDNs expressed other neuronal markers such as NeuN, GAP-43, PSD-95, AMPA receptors, Dopamine 1 receptors and Tyrosine Hydroxylase (data not shown).

Western Blot and Optical density per region assessments showed also that monocytes did not express the neuronal markers Nestin, MAP-2 and Neurofilament, while these neuronal markers were expressed by pluripotent macrophages (FIG. 6). Most importantly, this showed that the expression of these markers significantly increased while the differentiation progressed into the neuronal phenotype (FIG. 6).

2.4. Differentiation Rates

In order to determine the percentage of pluripotent macrophages that differentiated into neuronal-like cells 70,496 cells from 30 individuals were characterized (FIG. 8).

It was previously shown that neurons in culture undergo different structural changes before becoming mature neurons with sophisticated shapes (FIG. 8). These stages include rounded cells, unipolar or bipolar cells with very short extensions, stellar cells with thick extensions and flated soma and finally cells with rounded soma and long thin extension that can be unipolar, bipolar or stellar (Da Silva et al., 2002).

The inventors thus classified cells according to the shape they acquired at day 20 of the differentiation process, as follows.

i. cells with a rounded shape, or with a shape that did not match the structural changes observed during the developing process of a neuron as identified by Da Silva et al. (2002), were characterized as non-differentiated cells;

ii. cells with rounded somas, short unipolar or bipolar extensions were characterized as short unipolar/bipolar differentiated cells;

iii. cells with a flat soma and multiple thick extensions, were characterized as thick stellar (i.e. multipolar) differentiated cells;

iv. cells with rounded soma and long thin unipolar or bipolar extensions were characterized as long unipolar/bipolar differentiated cells; and finally v. cells with rounded soma and three or more thin long extensions were characterized as thin stellar (i.e. multipolar) differentiated cells.

At day 20, it was estimated that about 40% of the cultured cells differentiated into neuronal-like cells as defined herein.

3. Conclusions

The present method allows the differentiation of pluripotent macrophages derived from blood circulating monocytes into neuronal-like cells, in a consistent and reliable manner and in a short time period. These neuronal-like cells, characterized herein as macrophage-derived-neuronal-like cells (MDNs), structurally resemble neurons, present spontaneous electrical activity and express a variety of neuronal markers.

Preliminary results also indicated that MDNs generated according to the present method from monocytes cells isolated from schizophrenic patients could replicate at least some of the defects usually observed in the brains of these patients, such as a decrease in dopamine receptor 1 as reported by PET scans of living patients (Okubo et al, Nature, 1997) (see FIG. 9).

REFERENCES

Ruschenschmidt C., Koch P. G., Brüstle O., and Beck H. (2005). *Epilepsia* 46 (Suppl. 5), 174-183.

Zhao Y., Glesne D., and Huberman E. (2003). *Proc. Natl. Acad. Sci. USA;* 100(5): 2426-2431.

Kodama H., Inoue T., Watanabe R., Yasutomi D., Kawakami Y., Ogawa S., Mikoshiba K., Ikeda Y., and Kuwana M. (2006). *Immunol. Cell. Biol.;* 84(2): 209-217.

Freshney R. I. (2010). Culture of Animal Cells: A Manual of Basic Technique and Specialized Applications, 6th Edition, Wiley-Blackwell.

Wiles M. V. (1993). *Meth. Enzymol.;* 225:900.

Seta N. and Kuwana M. (2010). *Exp. Hematol.;* 38(7):557-63.

Martin J. H. (2012). Neuroanatomy Text and Atlas, 4th Edition.

Blumenfeld H. (2011). Neuroanatomy Through Clinical Cases, 2nd Edition, Sinauer Associates, Inc. Palay S. L. and Chan-Palay V. (1977). General Morphology of Neurons and Neuroglia, in *Comprehensive Physiology*, Wiley-Blackwell.

Da Silva J. S. and Dotti C. G. (2002). *Nat. Rev. Neurosci.;* 3:694-704.

Levitan I. B., Maloney D. J., and Kaczmarek L. K. (2001). *The Neuron: Cell and Molecular Biology: Cell and Molecular Biology.* Oxford University Press.

Ying H. S., Gottron F. J., Choi D. W. (2001). UNIT 7.18 Assessment of Cell Viability in Primary Neuronal Cultures. *Current Protocols in Neuroscience.*

Aras M. A., Hartnett K. A., and Aizenman E. (2008). UNIT 7.18 Assessment of Cell Viability in Primary Neuronal Cultures. *Current Protocols in Neuroscience.*

Fuss I. J., Kanof M. E., Smith P. D., and Zola H. (2009). *Curr. Protoc. Immunol.* Chapter 7: Unit7.1.

Lanza F., Healy L., and Sutherland D. R. (2001). *J. Biol. Regul. Homeost. Agents;* 15(1):1-13.

Grassi F., Dezutter-Dambuyant C., McIlroy D., Jacquet C., Yoneda K., Imamura S., Boumsell L., Schmitt D., Autran B., Debré P., and Hosmalin A (1998). *J. Leukoc. Biol.;* 64(4):484-93.

Feng D. D., Yang S. K., Loudes C., Simon A., Al-Sarraf T., Culler M., Alvear-Perez R., Llorens-Cortes C., Chen C., Epelbaum J., and Gardette R. (2011). *Eur. J. Neurosci.;* 34(5):732-44.

Aldridge G. M., Podrebarac D. M., Greenough W. T., and Weiler I. J. (2008). *J. Neurosci. Methods.* 172(2):250-254.

Okubo Y., Suhara T., Suzuki K., Kobayashi K., Inoue O., Terasaki O., Someya Y., Sassa T., Sudo Y., Matsushima E., Iyo M., Tateno Y., Toru M. (1997). *Nature;* 385(6617): 634-6.

The invention claimed is:

1. A method for in vitro differentiation of a population of pluripotent macrophages into a population of functional neuronal-like cells, wherein:
   1) a population of pluripotent macrophages is grown in a culture medium; and
   2) exogenous factors BHA (Butylated hydroxyanisole), RA (Retinoic Acid), IGF-1 (Insulin growth factor-1), and NT-3 (Neurotrophin) are added to the culture medium of step 1),
      wherein said pluripotent macrophages express the CD11B and CD14 surface antigen markers.

2. The method according to claim 1, comprising the prior step of differentiating a population of monocytes into a population of pluripotent macrophages.

3. The method according to claim 1, comprising the prior step of differentiating a population of monocytes into a population of pluripotent macrophages,
   wherein the differentiation of said population of monocytes into said population of pluripotent macrophages is obtained by:
      a) growing a population of monocytes in a culture medium; and
      b) adding the exogenous factor M-CSF (Macrophage colony-stimulating factor) to the medium of step a).

4. The method according to claim 1, wherein the exogenous factors of step 2) are sequentially added to the culture medium of step 1), in the following order:
   i) BHA (Butylated hydroxyanisole);
   ii) RA (Retinoic acid); and
   iii) IGF-1 (Insulin growth factor-1) and NT-3 (Neurotrophin-3).

5. The method according to claim 4, further comprising the step of: iv) adding at least one agent capable of stimulating calcium influx to the medium of step iii).

6. The method according to claim 4, wherein the BHA (Butylated hydroxyanisole) final concentration in step i) is comprised between about 50 nM and about 200 nM.

7. The method according to claim 4, wherein the RA (Retinoic Acid) final concentration in step ii) is comprised between about 10 µM and about 20 µM.

8. The method according to claim 4, wherein:
   the IGF-1 (Insulin growth factor-1) final concentration in step iii) is comprised between about 5 ng/ml and about 250 ng/ml; and
   the NT-3 (Neurotrophin-3) final concentration in step iii) is of up to about 30 ng/ml.

9. The method according to claim 4, wherein said BHA (Butylated hydroxyanisole) final concentration is adjusted before step iii) to a concentration comprised between about 50 µM and about 100 µM.

* * * * *